US011530440B2

(12) United States Patent
Blainey et al.

(10) Patent No.: US 11,530,440 B2
(45) Date of Patent: *Dec. 20, 2022

(54) METHODS FOR QUANTITATING DNA USING DIGITAL MULTIPLE DISPLACEMENT AMPLIFICATION

(71) Applicants: The Broad Institute, Inc., Cambridge, MA (US); Massachusetts Institute of Technology, Cambridge, MA (US)

(72) Inventors: Paul Blainey, Cambridge, MA (US); Liyi Xu, Cambridge, MA (US)

(73) Assignees: The Broad Institute, Inc., Cambridge, MA (US); Massachusetts Institute of Technology, Cambridge, MA (US)

( * ) Notice: Subject to any disclaimer, the term of this patent is extended or adjusted under 35 U.S.C. 154(b) by 33 days.

This patent is subject to a terminal disclaimer.

(21) Appl. No.: 16/673,018

(22) Filed: Nov. 4, 2019

(65) Prior Publication Data

US 2020/0063198 A1 Feb. 27, 2020

Related U.S. Application Data

(63) Continuation of application No. 14/851,945, filed on Sep. 11, 2015, now Pat. No. 10,487,354, which is a continuation-in-part of application No. PCT/US2014/028941, filed on Mar. 14, 2014.

(60) Provisional application No. 61/782,826, filed on Mar. 14, 2013.

(51) Int. Cl.
*C12P 19/34* (2006.01)
*C12Q 1/6851* (2018.01)

(52) U.S. Cl.
CPC ................... *C12Q 1/6851* (2013.01)

(58) Field of Classification Search
CPC .................................................. C12Q 1/6851
See application file for complete search history.

(56) References Cited

U.S. PATENT DOCUMENTS

| | | | |
|---|---|---|---|
| 5,616,478 | A | 4/1997 | Chetverin et al. |
| 5,856,145 | A | 1/1999 | Down et al. |
| 7,041,481 | B2 | 5/2006 | Anderson et al. |
| 7,473,551 | B2 | 1/2009 | Warthoe |
| 7,708,949 | B2 | 5/2010 | Stone et al. |
| 2005/0048581 | A1 | 3/2005 | Chiu et al. |
| 2005/0172476 | A1 | 8/2005 | Stone et al. |
| 2007/0195127 | A1 | 8/2007 | Ahn et al. |
| 2008/0003142 | A1 | 1/2008 | Link et al. |
| 2008/0014589 | A1 | 1/2008 | Link et al. |
| 2010/0137163 | A1 | 6/2010 | Link et al. |
| 2010/0172803 | A1 | 7/2010 | Stone et al. |
| 2011/0000560 | A1 | 1/2011 | Miller et al. |
| 2011/0118151 | A1 | 5/2011 | Eshoo et al. |
| 2011/0166845 | A1 | 7/2011 | Von Törne et al. |
| 2016/0068899 | A1 | 3/2016 | Blainey et al. |

FOREIGN PATENT DOCUMENTS

| | | |
|---|---|---|
| EP | 2047910 A2 | 4/2009 |
| WO | 2004002627 A2 | 1/2004 |
| WO | 2007089541 A2 | 8/2007 |
| WO | 2014153071 A1 | 9/2014 |

OTHER PUBLICATIONS

Baker, Monya, "Digital PCR Hits its Stride," Nature Methods, Jan. 1, 2012, retrieved from the Internet: URL: http://www.nature.com/nmeth/journal/v9/n6/pdf/nmeth.2027.pdf; retrieved on Jul. 29, 2014.
Blainey et al., "Digital MDA for Enumeration of Total Nucleic Acid Contamination," Nucleic Acids Research, Nov. 11, 2010; vol. 39, No. 4, pp. 1-9.
Blainey, Paul C. "The Future is Now: Single-Cell Genomics of Bacteria and Archaea," FEMS Microbiology Reviews, Feb. 11, 2013; vol. 37, No. 3, pp. 407-427.
Hindson et al., "High-Throughout Droplet Digital PCR System for Absolute Quanitifcation of DNA Copy Number," Analytical Chemistry, Nov. 15, 2011; vol. 83, No. 22, pp. 8604-8610.
International Preliminary Report on Patentability and Written Opinion dated Sep. 24, 2015, which issued during prosecution of International Application No. PCT/US2014/028941.
Morinishi et al., "Single-Molecule Counting by Whole Genome Amplification in a Microfluidic System," May 8, 2013, retrieved from the Internet: URL: http://web.mit.edu/leanna/www/20130508LM.pdf; retrieved Jul. 29, 2014.
Aviel-Ronen et al., "Large fragment Bst DNA polymerase for whole genome amplification of DNA from formalin-fixed paraffin-embedded tissues," BMC Genomics, Dec. 12, 2006, vol. 7, No. 312, pp. 1-10.
Blanco et al., "Characterization and purification of a phage θ29-encoded DNA polymerase required for the initiation of replication," Proceedings of the National Academy of Sciences of the United States of America, Sep. 1984, vol. 81, pp. 5325-5329.
Blanco et al., "Highly Efficient DNA Synthesis by the Phage θ29 DNA Polymerase," The Journal of Biological Chemistry, May 25, 1989, vol. 264, No. 15, pp. 8935-8940.
Dean et al., "Comprehensive human genome amplification using multiple displacement amplification," Proceedings of the National Academy of Sciences of the United States of America, Apr. 16, 2002, vol. 99, No. 8, pp. 5261-5266.
Dean et al., "Rapid Amplification of Plasmid and Phage DNA Using Phi29 DNA Polymerase and Multiply-Primed Rolling Circle Amplification," Genome Research, 2001, vol. 11, pp. 1095-1099.

(Continued)

*Primary Examiner* — Kenneth R Horlick
(74) *Attorney, Agent, or Firm* — Melissa Hunter-Ensor; Nicholas R. Ballor; Greenberg Traurig, LLP

(57) ABSTRACT

The present invention relates to methods of quantifying, amplifying, or preparing nucleic acid molecules, where the methods involve contacting a sample to be tested with nucleic acid molecule amplification reaction components and a label to form a reaction sample. The methods further involve partitioning the reaction sample into droplets or a gel and allowing nucleic acid molecule amplification to occur.

24 Claims, 10 Drawing Sheets

(56) References Cited

OTHER PUBLICATIONS

Evrony et al., "Single-Neuron Sequencing Analysis of L1 Retrotransposition and Somatic Mutation in the Human Brain," Cell, Oct. 26, 2012, vol. 151, pp. 483-496.

Kvist et al., "Specific single-cell isolation and genomic amplification of uncultured microorganisms," Applied Microbiology and Biotechnology, 2007, vol. 74, pp. 926-935.

Leung et al., "A programmable droplet-based microfluidic device applied to multiparameter analysis of single microbes and microbial communities," Proceedings of the National Academy of Sciences of the United States of America, May 15, 2012, vol. 109, No. 20, pp. 7665-7670.

Marcy et al., "Dissecting biological 'dark matter' with single-cell genetic analysis of rare and uncultivated TM7 microbes from the human mouth," Proceedings of the National Academy of Sciences of the United States of America, Jul. 17, 2007, vol. 104, No. 29, pp. 11889-11894.

Marcy et al., "Nanoliter Reactors Improve Multiple Displacement Amplification of Genomes from Single Cells," PLoS Genetics, Sep. 2007, vol. 3, No. 9, e155, pp. 1702-1708.

Mellado et al., "The Protein Covalently Linked to the 5' Termini of the DNA of Bacillus subtilis Phage θ29 is Involved in the Initiation of DNA Replication," Virology, 1980, vol. 104, pp. 84-96.

Morin et al., "Active DNA unwinding dynamics during processive DNA replication," Proceedings of the National Academy of Sciences of the United States of America, May 22, 2012, vol. 109, No. 21, pp. 8115-8120.

Raghunathan et al., "Genomic DNA Amplification from a Single Bacterium," Applied and Environmental Microbiology, Jun. 2005, vol. 71, No. 6, pp. 3342-3347.

Stepanauskas et al., "Matching phylogeny and metabolism in the uncultured marine bacteria, one cell at a time," Proceedings of the National Academy of Sciences of the United States of America, May 22, 2007, vol. 104, No. 21, pp. 9052-9057.

Woyke et al., "Decontamination of MDA Reagents for Single Cell Whole Genome Amplification," PLoS One, Oct. 2011, vol. 6, No. 10, e26161, pp. 1-5.

Zhang et al., "Ramification Amplification: A Novel Isothermal DNA Amplification Method," Molecular Diagnosis, 2001, vol. 6, No. 2, pp. 141-150.

Zhang et al., "Sequencing genomes from single cells by polymerase cloning," Nature Biotechnology, Jun. 2006, vol. 24, No. 6, pp. 680-686.

International Search Report and Written Opinion dated Aug. 12, 2014 in International Patent Application No. PCT/US2014/028941.

| Picking Preparation | Picking | Deposit | Settings |

- Properties of depositing in well
  - Speed Dispensing:
  - Waiting time after dispensing in s: 1
  - Amount of Airgap dispensed in target well:

- ☑ Rinse after depositing
- Rinse after depositing properties
  - Rinse amount in µl: 1
  - Amount of rinsing loops: 5
  - Speed Aspirating:
  - Speed Dispensing:

- Plate related properties
  - Direction of deposit
    - ● Horizontal - row by row
    - ○ Vertical - column by column
  - Offset to standard height at target well in mm: 9
  - Warning! Inappropriate values can seriously damage your device and the tools mounted on it. Please ask your ALS Automated Lab Solutions representative for advice if unsure.
  - ☐ Use tool sensor to determine plate base at deposit

- Max. amount of particle deposits per well: 1
- No. of targets to distribute particles to: 1

FIG. 7C

| Picking Preparation | Picking | Deposit | Settings |

- Volume of currently used syringe: 50 µl
- Time Limit for usage of source plate in min: 0
- Sterilisation Properties
  - Rinse amount at sterilisation in µl: 3
  - Amount of rinsing loops at sterilisation: 2
  - Waiting time in sterilisation liquid in s: 5
  - Waiting time for drying in s: 5

FIG. 7D

METHODS FOR QUANTITATING DNA USING DIGITAL MULTIPLE DISPLACEMENT AMPLIFICATION

RELATED APPLICATIONS AND INCORPORATION BY REFERENCE

This application is a continuation of U.S. Ser. No. 14/851,945, filed on Sep. 11, 2015, now issued U.S. Pat. No. 10,487,354, which is a continuation-in-part of international patent application Serial No. PCT/US2014/028941, filed Mar. 14, 2014 and published as PCT Publication No. WO 2014/153071 on Sep. 25, 2014 and which claims benefit of and priority to U.S. provisional patent application Ser. No. 61/782,826 filed Mar. 14, 2013. These applications each of which is incorporated in reference in their entirety.

FEDERAL FUNDING LEGEND

This invention was made with government support under Grant No. R01HG004863 awarded by the National Institutes of Health. The government has certain rights in the invention.

The foregoing application, and all documents cited therein or during their prosecution ("appln cited documents") and documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

FIELD OF THE INVENTION

The present invention relates to methods for quantitating nucleic acids, advantageously double stranded nucleic acids, such as double stranded DNA.

BACKGROUND OF THE INVENTION

Single-gene studies, metagenomic assemblies, and the genome sequences of a limited number of cultured isolates are not a sufficient basis on which to accurately model the responses of natural microbial networks or engineer the function of artificial communities. For example, gene catalogs and composite genomes assembled from metagenomic data do not presently distinguish between genes that are tightly coupled within the context of the same organism and genes that are coupled across different organisms. This is a critical limitation, because only gene products encoded by the same organism can freely come into contact with one another to form complexes, drive signaling pathways, or carry out multi-step enzymatic transformations of diffusible substrates at maximum efficiency. A systems-level predictive understanding of microbial physiology absolutely demands the interpretation of genes and pathways in a full genomic context. Furthermore, individual organisms (indeed single cells) encoding full genomes are the basic replicating unit of biology and an important unit of evolutionary selection, factors that cannot be ignored in understanding the development of microbial networks in larger populations as a function of time.

In practical terms for single microbial cell sequencing, this means a million-fold amplification of the DNA present at the time of cell selection is required. Such high fold-amplification from sub-nanogram samples (Dean, et al., 2002, Proceedings of the National Academy of Sciences 99: 5261) and individual bacteria (Raghunathan, et al., 2005, Applied and Environmental Microbiology 71: 3342-3347) with good representation of the genome were first achieved by the multiple displacement amplification (MDA) whole-genome amplification (WGA) chemistry, but produced material with undesirable characteristics such as uneven representation and dislocated sequences. Nonetheless, investigators shortly succeeded in assembling shotgun sequence reads from single WGA-amplified *E. coli* and *Prochlorococcus* (Zhang, et al., 2006, Nat Biotechnol 24: 680-686), TM7 (Marcy, et al., 2007, Proc Natl Acad Sci USA 104: 11889-11894), and sequencing multiple genes from *E. coli* (Marcy, et al., 2007, PLoS Genet 3: 1702-1708), single marine bacteria (Stepanauskas & Sieracki, 2007, Proc Natl Acad Sci USA 104: 9052-9057), and soil and cultivated archaea (Kvist, et al., 2007, Applied microbiology and biotechnology 74: 926-935). Since the development of MDA, many other WGA methods have been developed and successfully applied to single cells (Blainey 2013, Cai & Walsh et al, 2012).

MDA is the WGA method that has been most commonly applied in single-cell sequencing of microbes. MDA works by the extension of 6-mer 3'-protected random primers on the DNA template (Dean, et al., 2001, Genome Res 11: 1095-1099). In MDA, a polymerase with strong strand displacement activity such as phi29 DNA polymerase or Bst DNA polymerase creates and displaces overlapping synthesis products from the template as single-stranded DNA under isothermal conditions (Dean, et al., 2001, Genome Res 11: 1095-1099; Zhang, et al., 2001, Mol Diagn 6: 141-150; Aviel-Ronen, et al., 2006, BMC Genomics 7). The displaced single-stranded DNA is a substrate for further priming and synthesis (Dean, et al., 2001, Genome Res 11: 1095-1099; Zhang, et al., 2001, Mol Diagn 6: 141-150). Phi29 DNA polymerase is typically specified for MDA due to its high accuracy owing to 3'-5' exonuclease-mediated proofreading and exceptionally strong processivity in strand displacement synthesis, which can exceed 10,000 nt (Mellado, et al., 1980, Virology 104: 84-96; Blanco & Salas, 1984, Proceedings of the National Academy of Sciences 81: 5325; Blanco, et al., 1989, Journal of Biological Chemistry 264: 8935-8940; Morin, et al., 2012, Proceedings of the National Academy of Sciences 109: 8115-8120). This property of the polymerase evens out amplification on shorter genomic distances to produce high molecular weight products with more uniform amplification across the template than purely PCR-based methods, which typically produce products shorter than 1000 nt and exhibit greater amplification bias (Dean, et al., 2002, Proceedings of the National Academy of Sciences 99: 5261). In late 2012, one vendor started marketing a MDA kit that is decontaminated with ultraviolet light treatment and includes a mutant enzyme claimed to improve amplification uniformity and chimera performance (Qiagen REPLI-g Single Cell).

Given the concentration of contaminating fragments present in commercial WGA reagents (varying from 5 to 50 fragments per reaction microliter in the enzyme alone), volume reduction by itself does not necessarily eliminate reagent contamination (Blainey & Quake, 2011, Nucleic Acids Res 39: e19). For example, even driving reaction volumes down to the low nanoliter range, a significant fraction of reactions are still expected to carry contaminates from the reagents. Thus it is necessary to either inactivate contaminates in the reagents or produce reagent sets that are free of contamination. Contaminates in commercial WGA kits have been successfully suppressed by UV exposure with acceptable post-treatment amplification performance (Zhang, et al., 2006, Nat Biotechnol 24: 680-686; Woyke, et al., 2011, Plos One 6: e26161). Alternatively, reagents for background-free WGA can be produced in batch processes utilizing disposable plasticware produced from virgin materials (Blainey & Quake, 2011, Nucleic Acids Res 39: e19). Irrespective of the clean-up approach taken, a key capability for validating reagent lots and clean-up procedures is a rapid assay for WGA activity and contamination. To be useful, the contamination assay must be both quantitative and extremely sensitive, such that different lots or treatments can be evaluated comparatively. QPCR is insufficiently sensitive since only contaminant molecules with an intact sequence locus matching specific PCR primers can be detected. For example, a PCR assay for the small subunit ribosomal RNA gene misses thousands of contaminant fragments arising from bacterial genomic DNA for every fragment molecule detected. Alternatively, the digital WGA (dWGA, eg digital MDA or dMDA) assay can be used for quantitation down to a few attograms of degraded genomic DNA per microliter (Blainey & Quake, 2011, Nucleic Acids Res 39: e19). dWGA is compatible with a variety of off-the-shelf platforms engineered for digital PCR (Baker, 2012, Nature methods 9: 541-544).

There is a need for improved methods for detecting contamination in reagents as well as improved methods for quantitating DNA.

Citation or identification of any document in this application is not an admission that such document is available as prior art to the present invention.

SUMMARY OF THE INVENTION

This invention fulfills a need for improved methods for detecting contamination in WGA reagents as well as improved methods for quantitating DNA.

Technological advances improve the reliability and throughput of single-cell WGA and sequencing. The contamination of reagents with bacterial DNA that plagued early efforts in single-cell microbial genomics is now well-understood, and effective measures to quantify, control, and eliminate such contamination are disclosed herein. The elimination of background amplification not only yields clean datasets, but also allows the facile application of screens for successful WGA reactions. The move to lower-volume WGA reaction platforms further reduces the impact of contaminates and WGA reagent costs, opening the way to massive increases in reaction throughput.

The key drivers of new technology for single-cell genomics are advances in throughput, integration of isolation and WGA with selection and sequencing procedures, improvements in more uniform representation of template sequences in the WGA product, fewer artifact sequences such as chimeras, expanded sample/cell type compatibility, and contextualization of single-cell genome data by in-line collection of other information about the processed cells (eg phenotyping, imaging, RNA, protein, metabolite analyses). The ability to obtain sequence data from individual cells from a known biological setting or with a known history (e.g. interaction with other cells prior to the analysis) is especially informative. Because sample preparation costs already dominate single-cell microbial genomics workflows today, the most impactful advances will scale to large numbers of cells at reasonable cost.

The present invention relates to methods of quantifying nucleic acids which may comprise (a) contacting a sample to be tested with whole-genome amplification (WGA) reaction components and a dye molecule to form a reaction sample, wherein the dye molecule detects the nucleic acid; (b) partitioning the reaction sample wherein each partitioned reaction sample corresponds to a single reaction; (c) allowing the reaction to occur in the partitioned reaction sample and (d) determining the number of partitioned reaction samples having the dye molecule, wherein the dye molecule indicates the presence of the nucleic acid; thereby quantifying the nucleic acid is quantitated in the sample to be tested.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings.

FIG. 7A depicts a picking preparation. Glass capillary is preloaded with 1 ul of 2% PBST (PBS with the surfactant TWEEN™ 20) buffer with an air gap of 0.5 ul between the system oil.

FIG. 7B depicts picking. Tool sensor on was turned on, which detects the hard glass slide surface and signals glass capillary the right picking position. Capillary was elevated for 20 um before aspirating. 2 ul of hydrogel cylinder was retrieved in capillary for depositing.

FIG. 7C depicts deposit. The hydrogel cylinder was dispensed into a PCR 96 tube well filled with 10 ul of lysis buffer. Maximum air gap was dispensed and the capillary was rinsed 5 times to ensure complete dispensing.

FIG. 7D depicts setting. After picking and depositing, the capillary is sterilized with 3 ul of 2% PBST for 2 loops with a 5 sec of waiting time in between.

DETAILED DESCRIPTION OF THE INVENTION

Figure 1:
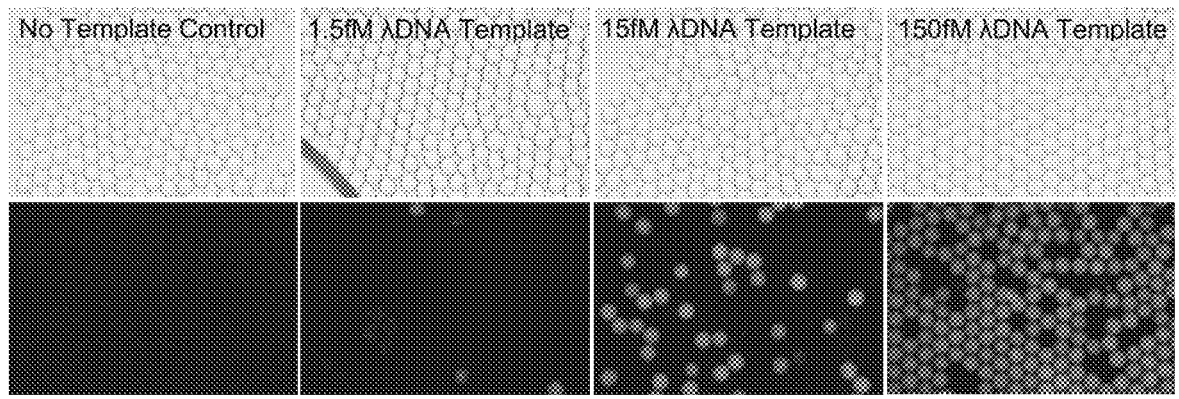
FIG. 1 depicts MDA reactions with appropriate template concentrations were prepared using a Qiagen Repli-G Midi kit according to the manufacturer's protocol (Qiagen, Valencia, Calif.), and supplemented with the DNA dye EVAGREEN™. Monodisperse droplets were formed in a flow-focusing microfluidic device with fluorinated oil continuous phase and incubated at 30 C for 16 h.

The present invention relates to methods of quantifying a nucleic acid which may comprise (a) contacting a sample to be tested with whole-genome amplification (WGA) reaction components and a dye molecule to form a reaction sample, wherein the dye molecule detects the nucleic acid; (b) partitioning the reaction sample wherein each partitioned reaction sample corresponds to a single reaction; (c) allowing the reaction to occur in the partitioned reaction sample and (d) determining the number of partitioned reaction samples having the dye molecule, wherein the dye molecule indicates the presence of the nucleic acid; thereby quantifying the nucleic acid is quantitated in the sample to be tested.

Although dsDNA is a preferred substrate for quantitation, the invention may be extrapolated to any nucleic acid, such as ssDNA, RNA, or PNA. The nucleic acid may be advantageously a double stranded nucleic acid, such as double-stranded DNA (dsDNA) or double-stranded RNA (dsRNA). In other embodiments, the nucleic acid is a single stranded nucleic acid, such as single stranded DNA (ssDNA) or RNA. In yet other embodiments, the nucleic acids may be labeled using a natural or engineered nucleoside or a nucleotide. In another embodiment, the nucleic acid may be labeled using a nucleic acid probe. In still another embodiment, the nucleic acid or probe is a peptide nucleic acid (PNA).

WGA is an area of active development with a long history. Several approaches were developed, all based on synthesis by DNA polymerase with various priming strategies that utilize specific, degenerate, and/or hybrid primers. Single microbial cell WGA was prosecuted almost exclusively by one method, multiple displacement amplification (MDA). This is particularly interesting since a variety of methods have been successfully applied to single-cell WGA of mammalian cells and ongoing development of WGA methods appears to be more active in WGA methods based on degenerate oligonucleotide primed PCR (DOP-PCR). Over the next few years, it is likely that WGA procedures with improved characteristics and new capabilities will be introduced based on different strategies. Because of the necessity to match amplification chemistry to sorting and lysis procedures and the potential benefit of new single-cell WGA methods for microbiological studies, it is useful to review existing WGA methodologies here in a comprehensive manner.

Two early WGA methods were based on PCR with specific primers. In linker-adapter (also known as ligation-anchored) PCR (LA-PCR), adapter oligonucleotides containing specific PCR priming sites are ligated to sheared template fragments, which are then amplified by PCR] (Troutt, et al., 1992, Proceedings of the National Academy of Sciences 89: 9823; Klein, et al., 1999, Proc Natl Acad Sci USA 96: 4494-4499). Interspersed repetitive sequence PCR (IRS-PCR) takes a different approach by targeting previously characterized repeating sequence elements with specific primers (Haberhausen, 1987, PCR: Overview on Application Formats in Research and Clinical Diagnosis. Vol. 289), p. 327. Springer Verlag; Ledbetter, et al., 1990, Genomics 6: 475; Lengauer, et al., 1990, Human genetics 86: 1-6; Lichter, et al., 1990, Proceedings of the National Academy of Sciences 87: 6634). This approach has been applied to alu repeats in human samples, for instance.

Other methods take advantage of degenerate oligonucleotide primers that obviate the need for ligation reactions or prior knowledge of the sequence to be amplified. Primer extension preamplification PCR (PEP-PCR) introduced degenerate primers for whole-genome PCR, applying 15-mer random oligonucleotides as PCR primers under permissive thermocycling conditions, in principle enabling priming at any location in the template sequence (Hubert, et al., 1992, American journal of human genetics 51: 985; Zhang, et al., 1992, Proceedings of the National Academy of Sciences 89: 5847). Degenerate oligonucleotide primed PCR (DOP-PCR) uses hybrid oligos with degenerate bases at some positions to allow dense priming of the template (Telenius, et al., 1992. Genomics 13: 718-725). Typically, DOP-PCR is run in two stages, with the first PCR stage facilitating primer extension on the template and the second PCR stage favoring amplicon replication. An interesting variant of DOP-PCR, referred to here as 'displacement DOP-PCR' (D-DOP-PCR, marketed as PicoPlex by Rubicon Genomics), was developed that allows strand displacement synthesis from hybrid primers during the first stage (in a fashion similar to MDA, described below), followed by the addition of specific primers that amplify the products of the first stage by PCR in the second stage (Langmore, 2002, Pharmacogenomics 3: 557-560). Despite extensive development, the D-DOP-PCR method has only recently been applied to WGA of individual microbes (Leung, et al., 2012, Proceedings of the National Academy of Sciences 109: 7665-7670).

In an advantageous embodiment, the WGA is carried out by multiple displacement amplification (MDA).

Multiple displacement amplification (MDA) is an isothermal, sequence-independent method for exponential amplification of high molecular weight DNA. MDA, which relies on the strong strand-displacement synthesis activity of φ29 DNAP, has revolutionized analyses of small-quantity DNA samples by providing a means to carry out high fidelity whole genome amplification while maintaining more uniform locus representation than competing techniques, especially those based on PCR. However, background amplification limits the application of MDA in the most demanding applications, i.e. for single-cell analysis, forensics and analysis of ancient samples.

There has been a debate in the art whether this background amplification arises from high molecular weight DNA contaminants and/or from side products of the MDA reaction derived from the random primers used. In the best case, background amplification merely reduces product yield. In other cases, downstream analyses based on product quantification, genotyping or sequencing may be compromised.

In previous work using MDA in microfluidic devices, where amplification reactions are carried out in small volumes, typically 60 nl, contaminating sequences have been observed in <10% of nanoliter single-cell amplifications, suggesting that the concentration of contaminating molecules in the MDA reaction mix was lower than one per 60 nl. However, over a period of about a year, an increase in levels of bacterial DNA contaminating the commercial MDA reagents was noticed. After changing suppliers several times and continuing to experience high levels of reagent contamination, Blainey and Quake (Nucleic Acids Research, 2010, 1-9) set out to create their own 'high-purity' MDA reagent set and to develop an assay to measure contaminant levels directly. Blainey and Quake found standard PCR methods (including digital PCR) relying on the 16S small subunit ribosomal RNA (ssu rRNA) gene locus to be inadequate, and developed a new method, digital MDA (or dMDA), for direct, quantitative, measurement of contaminating DNA fragments with extremely high sensitivity.

Single primer isothermal amplification (SPIA) is an isothermal strand-displacement based method that utilizes partially degenerate primers which contain a specific sequence of RNA nucleotides (Kurn, et al., 2005, Clinical Chemistry 51: 1973-1981). An RNA/DNA primer, together with RNAse H activity and a strand-displacing DNA polymerase work together to achieve linear amplification under isothermal conditions, where the DNA polymerase extends the primer with DNA bases and displaces earlier product molecules and RNAse H activity degrades the RNA portion of the primer to expose the priming site and allow interaction with another primer molecule for subsequent synthesis. The product molecules are not templates for the RNA/DNA primer in this stage, preventing chain reaction (exponential) synthesis.

A new method called Multiple Annealing and Looping Based Amplification Cycles (MALBAC) was recently demonstrated on individual human cells (Xie et al, Science in press). The structure of the partially degenerate hybrid primers used in MALBAC is similar to that in D-DOP-PCR, but the sequence of their constant regions is designed to work in concert with thermal cycling during the initial reaction stage to enforce linear amplification of the original template. This is accomplished by allowing products of an initial strand displacement synthesis step to be copied and to form loops by hybridization of complementary sequences on their 3' and 5' ends. This looping prevents doubly-tagged products from priming further synthesis or acting efficiently as templates for further synthesis under the conditions for sub-exponential amplification. After several rounds of thermocycled linear amplification in which priming biases are partially washed out, the thermal program is altered to enable conventional PCR amplification. In the demonstration with human cells, the MALBAC amplification was more uniform than control MDA reactions.

Single-cell WGA applications are far more sensitive to amplification bias and the formation of artificial chimeras (hereafter, simply 'chimeras') than multi-cell reactions. With respect to bias, multi-cell bulk WGA reactions suffer from systematic biases such as sequence-dependent priming efficiencies and primer extension rates, but stochastic variations in WGA reaction sub-steps are evened out, since many copies of each locus are present. On the other hand, single-cell WGA can depend on as few as one or two (double-stranded or single-stranded) copies of each locus as template, and is susceptible to the random bias effects as a result. The magnitude of the random bias typically dominates systematic biases driven by sequence content in single-cell WGA applications. Some protocols for PCR-based WGA call for fragmentation of the sample prior to amplification. This practice is not recommended for a number of single-cell WGA applications, as no sequences spanning these original break points will be present in the mixture of products.

Reduced WGA reaction volume and low-shear microfluidic sample handling not only reduce contamination of single-cell WGA products, but have also been associated with improved genomic coverage for the MDA chemistry (Marcy, et al., 2007, PLoS Genet 3: 1702-1708), although the relative contributions of lysis quality, reduced DNA shearing during mixing, reduced competition from contaminants, altered reagent stability, and unknown factors to this effect have yet to be systematically investigated.

Chimeric sequences are formed as artifacts in strand displacement-driven and PCR-based DNA amplification reactions when synthesis products prime further synthesis by 'inappropriately' hybridizing with the template material or product molecules (Zhang, et al., 2006, Nat Biotechnol 24: 680-686; Lasken & Stockwell, 2007, BMC biotechnology 7: 19). The fraction of molecules in the mixture of products carrying these chimeras can be significant, often exceeding 10%, and exceeding 50% in some cases (Wang & Wang, 1996, Microbiology 142: 1107-1114; Zhang, et al., 2006, Nat Biotechnol 24: 680-686). Chimeras link template sequences that are not adjacent in the original template, creating artifacts that can be extremely disruptive to downstream analyses. Analogous to the case for amplification bias, the limited copy number of loci in the original template for single-cell WGA reactions aggravates the problem, because when further amplified, chimeras can dominate the product mixture at specific loci. In de novo applications, such chimeric sequences are likely to be accepted in reconstructions of the true sequence, corrupting the dataset.

Particularly in small-volume reaction configurations, higher WGA product concentration can be advantageous in the context of the whole sequencing workflow. MDA stands out in this respect as capable of producing single-cell product concentrations up to an order of magnitude higher than PCR-based WGA methods. In MDA, the single-stranded template for priming and synthesis is produced under the priming (annealing) condition, and primers do not compete directly with amplified product molecules for template hybridization and enzyme, factors which, among others, have been implicated in causing the plateau phase of PCR reactions (Morrison & Gannon, 1994, Biochimica et Biophysica Acta (BBA)-Gene Structure and Expression 1219: 493-498; Kainz, 2000, Biochimica et Biophysica Acta (BBA)-Gene Structure and Expression 1494: 23-27). PCR-based WGA methods are limited by this product inhibition effect and typically produce DNA at concentrations of 50-100 ng/microliter, with the exception of the comparatively inefficient PEP-PCR method, which has been reported to produce relatively low-fold amplification in reactions with small numbers of cells (Zhang, et al., 1992, Proceedings of the National Academy of Sciences 89: 5847; Sun, et al., 1995, Nucleic Acids Research 23: 3034-3040; Dietmaier, et al., 1999, The American journal of pathology 154: 83-95).

Few systematic comparisons of the various chemistries for WGA have been carried out, and none that comprehensively address amplification-fold, bias, replication errors, and the incidence of chimerism, or that have been implemented in the low-volume formats that are advantageous for single-cell WGA. Side-by-side comparisons of single-cell WGA are necessary to overcome confounding variability in cell preparation, handling, lysis, and approaches to implementing small-volume WGA reactions. Progress in the field is limited for a lack of such comparisons, leaving investigators uncertain about which approach to take, what factors are critical in implementation, and whether observed results constitute typical performance of a given chemistry.

Given the concentration of contaminating fragments present in commercial WGA reagents (varying from 5 to 50 fragments per reaction microliter in the enzyme alone), volume reduction by itself does not necessarily eliminate reagent contamination (Blainey & Quake, 2011, Nucleic Acids Res 39: e19). For example, even driving reaction volumes down to the low nanoliter range, a significant fraction of reactions are still expected to carry contaminates from the reagents. Thus it is necessary to either inactivate contaminates in the reagents or produce reagent sets that are free of contamination. Contaminates in commercial WGA kits have been successfully suppressed by UV exposure with acceptable post-treatment amplification performance (Zhang, et al., 2006, Nat Biotechnol 24: 680-686; Woyke, et al., 2011, Plos One 6: e26161). Alternatively, reagents for background-free WGA can be produced in batch processes utilizing disposable plasticware produced from virgin materials (Blainey & Quake, 2011, Nucleic Acids Res 39: e19). Irrespective of the clean-up approach taken, a key capability for validating reagent lots and clean-up procedures is a rapid assay for WGA activity and contamination. To be useful, the contamination assay must be both quantitative and extremely sensitive, such that different lots or treatments can be evaluated comparatively. QPCR is insufficiently sensitive since only contaminant molecules with an intact sequence locus matching specific PCR primers can be detected. For example, a PCR assay for the small subunit ribosomal RNA gene misses thousands of contaminant fragments arising from bacterial genomic DNA for every fragment molecule detected. Alternatively, the digital WGA (dWGA, eg digital MDA or dMDA) assay can be used for quantitation down to a few attograms of degraded genomic DNA per microliter (Blainey & Quake, 2011, Nucleic Acids Res 39: e19). dWGA is compatible with a variety of off-the-shelf platforms engineered for digital PCR (Baker, 2012, Nature methods 9: 541-544).

In an advantageous embodiment, the MDA reaction components may be from a commercial MDA, such as but not limited to, Repli-G Midi (Qiagen), GenomiPhi (GE) and RepliPHI (Epicentre) and Repli-G Single Cell (Qiagen).

In another advantageous embodiments, the WGA reaction components may also include an emulsion component. The aqueous emulsion phase may be dispersed in an inert oil, such as but not limited to a fluorocarbon oil, perfluoropolyether, silicone oil, an inert oil such as hydrocarbon, or another oil (for example, mineral oil).

The sample fluid may typically comprise an aqueous buffer solution, such as ultrapure water (e.g., 18 mega-ohm resistivity, obtained, for example by column chromatography), 10 mM Tris HCl and 1 mM EDTA (TE) buffer, phosphate buffer saline (PBS) or acetate buffer. Any liquid or buffer in which nucleic acid molecules are soluble or chemically stable can be used. The carrier fluid may include one that is immiscible with the sample fluid. The carrier fluid can be a non-polar solvent, decane (e.g., tetradecane or hexadecane), fluorocarbon oil, silicone oil, an inert oil such as hydrocarbon, or another oil (for example, mineral oil).

In certain embodiments, the reaction mixture may be in a surfactant which may reduce the surface tension at the aqueous oil interface. Preferred surfactants that may be added to the reaction include, but are not limited to, surfactants such as sorbitan-based carboxylic acid esters (e.g., the "SPAN™" surfactants, Fluka Chemika), including sorbitan monolaurate (SPAN™ 20), sorbitan monopalmitate (SPAN™ 40), sorbitan monostearate (SPAN™ 60) and sorbitan monooleate (SPAN™ 80), and fluorinated and perfluorinated polyethers (e.g., DuPont Krytox 157 FSL, FSM, and/or FSH). Other non-limiting examples of non-ionic surfactants which may be used include polyoxyethylenated alkylphenols (for example, nonyl-, p-dodecyl-, and dinonylphenols), polyoxyethylenated straight chain alcohols, polyoxyethylenated polyoxypropylene glycols, polyoxyethylenated mercaptans, long chain carboxylic acid esters (for example, glyceryl and polyglyceryl esters of natural fatty acids, propylene glycol, sorbitol, polyoxyethylenated sorbitol esters, polyoxyethylene glycol esters, etc.) and alkanolamines (e.g., diethanolamine-fatty acid condensates and isopropanolamine-fatty acid condensates).

Other surfactants may also include, but are not limited to, those sold under the trade name TWEEN™, TRITON™, SPAN™, or PLURONIC™, a poly(ethylene glycol)-containing molecule or a perfluoropolyether-containing molecule. Advantageously, the surfactant is TWEEN™, preferably TWEEN™-20, more advantageously 0.3% TWEEN™-20.

The present invention involves partitioning the WGA reactions into separate reactions and allowing the reaction to proceed in each partition. The partitioning may occur in a droplet, such as a microemulsion droplet or a droplet on a surface, in a matrix, such as a gel, advantageously a hydrogel, in an emulsion or some other media allowing the segregating of template molecules and/or partitioning of the reactions. The invention also encompasses partitioning the WGA reactions in a microfluidic device, wherein the device subdivides the sample.

The partitioning may be by compartmentalization by immobilization in a matrix, such as a gel. If the reactions are partitioned in a matrix, such as a gel, then the dsDNA may be quantified by counting the number of labeled spots in a gel. The gel may be a hydrogel, advantageously a acrylate gel, more advantageously an acrylate-dithiol gel, in particular a PEG acrylate-dithiol hydrogel. If the partitions are in an aqueous solution, the samples may be combined and quantified in a fluorimeter or spectrophotometer, for example. See, e.g., FIGS. 3-6. The hydrogel may also comprise a polyethylene glycol, a peptide, a polysaccharide, a synthetic polymer, a natural polymer and/or a block copolymer or any combination thereof. The partitioning may be by compartmentalization by immobilization in a gel.

Advantageously, the reaction may be supplemented with the surfactant sold under the trade name TWEEN™ which may be TWEEN™-20, TWEEN™-60 or TWEEN™-80. The concentration of TWEEN™ may be about 0.1%, 0.2%, 0.3%, 0.4%, 0.5%, 0.6%, 0.7%, 0.8%, 0.9% or 1%. w/v %.

The reactions may be controlled by several parameters, such as temperature. The reaction may occur at about 20° C., 25° C., 30° C., 35° C., 40° C., 45° C., 50° C., 55° C., 60° C., 65° C., 70° C., 75° C., 80° C., 85° C., 90° C., 95° C. or about 100° C.

The present invention may provide a closed feedback control system for producing and manipulating a predetermined characteristic of a microfluidic droplet and the systematic combination of one or more droplet combinations with single or multiple cells. The invention described herein enables high throughput and high resolution delivery of reagents to individual emulsion droplets that may contain cells, nucleic acids, proteins, etc. through the use of monodisperse or polydisperse aqueous droplets that are generated one by one in a microfluidic chip as a water-in-oil emulsion or alternatively by a bulk process such as but not limited to mixing, entrainment, or extrusion. The droplets are suspended in an immiscible continuous phase such as but not limited to an oil and stabilized by a surfactant. In one aspect single cells or single molecules (proteins, RNA, DNA) are encapsulated into uniform droplets from an aqueous solution/dispersion with a rate up to a few kHz. In a related aspect, multiple cells or multiple molecules may take the place of single cells or single molecules. The aqueous droplets of volume ranging from 1 pL to 10 nL work as individual reactors. Disclosed embodiments provide that the droplets can be manipulated and measured at a rate of $10^8$ per day using droplet-based microfluidics.

To utilize microdroplets for rapid large-scale chemical screening or complex biological library identification, different species of microdroplets, each containing the specific chemical compounds or biological probes of interest, have to be generated and combined at the preferred conditions, e.g., mixing ratio and order of combination. For example as described in US patent publication no. 20110000560, one microdroplet of species A must be combined with one microdroplet of species B, but not with two microdroplets of species B or with one microdroplet of species C. The ratio of combining different species of microdroplets is achieved by adjusting the frequencies at which microdroplets are delivered to the site of combination. The terms "frequency" or "frequencies" refer to the rate at which microdroplets of certain species are delivered to a specific location. Moreover, this frequency or rate is a number per unit time, typically several hundred to tens of thousands per second. Furthermore the terms "frequency" or "frequencies" refers to the number of times at which droplets of certain species are delivered to a specific location. The location may be where certain behaviors of droplets (e.g., pairing, merging, combination, etc.) occur or where certain actions (e.g., electrification, mechanical deformation, etc.) are applied to droplets. Preferably, the location is where combination of droplets occurs.

Each species of droplet is introduced at a confluence point in a main microfluidic channel from separate inlet microfluidic channels. Preferably, droplet volumes are chosen by design such that one species is larger than others and moves at a different speed, usually slower than the other species, in the carrier fluid, as disclosed in U.S. Publication No. US 2007/0195127 and International Publication No. WO 2007/089541, each of which are incorporated herein by reference in their entirety. The channel width and length is selected such that faster species of droplets catch up to the slowest species. Size constraints of the channel prevent the faster moving droplets from passing the slower moving droplets resulting in a train of droplets entering a merge zone. In the merge zone, droplets are induced to coalesce into a single droplet, preferably an electric field is utilized to induce coalescence. Multi-step chemical reactions, biochemical reactions, or assay detection chemistries often require a fixed reaction time before species of different type are added to a reaction. Multi-step reactions are achieved by repeating the process multiple times with a second, third or more confluence points each with a separate merge point. Highly efficient and precise reactions and analysis of reactions are achieved when the frequencies of droplets from the inlet channels are matched to an optimized ratio and the volumes of the species are matched to provide optimized reaction conditions in the combined droplets.

Key elements for using microfluidic channels to process droplets include: (1) producing droplet of the correct volume, (2) producing droplets at the correct frequency and (3) bringing together a first stream of sample droplets with a second stream of sample droplets in such a way that the frequency of the first stream of sample droplets matches the frequency of the second stream of sample droplets. Preferably, bringing together a stream of sample droplets with a stream of premade library droplets in such a way that the frequency of the library droplets matches the frequency of the sample droplets.

Methods for producing droplets of a uniform volume at a regular frequency are well known in the art. One method is to generate droplets using hydrodynamic focusing of a dispersed phase fluid and immiscible carrier fluid, such as disclosed in U.S. Publication No. US 2005/0172476 and International Publication No. WO 2004/002627. Feedback on the infusion rates of the carrier fluid and the dispersed fluid provides droplets that are uniform in size and generated at a fixed frequency over arbitrarily long periods of time. However, sample to sample variations in viscosity, viscoelasticity, surface tension or other physical properties of the sample fluid coming from but not limited to the inclusion of polymers, detergents, proteins, cells, nucleic acids or buffering solutions, influence the droplet size, and, hence, frequency of generation in an unpredictable way, generating a significant problem to be solved. Hence, the same nozzle on the same substrate with same carrier fluid, but a different dispersed fluid will result in a different droplet volume at a different frequency. Moreover, often it is desirable for one of the species introduced at the confluence to be a pre-made library of droplets where the library contains a plurality of reaction conditions, e.g., a library may contain plurality of different compounds at a range of concentrations encapsulated as separate library elements for screening their effect on cells or enzymes, alternatively a library could be composed of a plurality of different primer pairs encapsulated as different library elements for targeted amplification of a collection of loci, alternatively a library could contain a plurality of different antibody species encapsulated as different library elements to perform a plurality of binding assays. The introduction of a library of reaction conditions onto a substrate is achieved by pushing a premade collection of library droplets out of a vial with a drive fluid. The drive fluid is a continuous fluid. The drive fluid may comprise the same substance as the carrier fluid (e.g., a fluorocarbon oil). For example, if a library consists of ten pico-liter droplets is driven into an inlet channel on a microfluidic substrate with a drive fluid at a rate of 10,000 pico-liters per second, then nominally the frequency at which the droplets are expected to enter the confluence point is 1000 per second. However, in practice droplets pack with oil between them that slowly drains. Over time the carrier fluid drains from the library droplets and the number density of the droplets (number/mL) increases. Hence, a simple fixed rate of infusion for the drive fluid does not provide a uniform rate of introduction of the droplets into the microfluidic channel in the substrate. Moreover, library-to-library variations in the mean library droplet volume result in a shift in the frequency of droplet introduction at the confluence point. Thus, the lack of uniformity of droplets that results from sample variation and oil drainage provides another problem to be solved. For example if the nominal droplet volume is expected to be 10 pico-liters in the library, but varies from 9 to 11 pico-liters from library-to-library then a 10,000 pico-liter/second infusion rate will nominally produce a range in frequencies from 900 to 1,100 droplet per second. In short, sample to sample variation in the composition of dispersed phase for droplets made on chip, a tendency for the number density of library droplets to increase over time and library-to-library variations in mean droplet volume severely limit the extent to which frequencies of droplets may be reliably matched at a confluence by simply using fixed infusion rates. In addition, these limitations also have an impact on the extent to which volumes may be reproducibly combined. Combined with typical variations in pump flow rate precision and variations in channel dimensions, systems are severely limited without a means to compensate on a run-to-run basis. The foregoing facts not only illustrate a problem to be solved, but also demonstrate a need for a method of instantaneous regulation of microfluidic control over microdroplets within a microfluidic channel.

In certain embodiments, the carrier fluid may contain one or more additives, such as agents which reduce surface tensions (surfactants). Surfactants can include those sold under the trade name TWEEN™ or SPAN™, or fluorosurfactants, and other agents that are soluble in oil relative to water. In some applications, performance is improved by adding a second surfactant to the sample fluid. Surfactants can aid in controlling or optimizing droplet size, flow and uniformity, for example by reducing the shear force needed to extrude or inject droplets into an intersecting channel. This can affect droplet volume and periodicity, or the rate or frequency at which droplets break off into an intersecting channel. Furthermore, the surfactant can serve to stabilize aqueous emulsions in fluorinated oils from coalescing.

Combinations of surfactant(s) and oils must be developed to facilitate generation, storage, and manipulation of droplets to maintain the unique chemical/biochemical/biological environment within each droplet of a diverse library. Therefore, the surfactant and oil combination must (1) stabilize droplets against uncontrolled coalescence during the drop forming process and subsequent collection and storage, (2) minimize transport of any droplet contents to the oil phase and/or between droplets, and (3) maintain chemical and biological inertness with contents of each droplet (e.g., no adsorption or reaction of encapsulated contents at the oil-water interface, and no adverse effects on biological or chemical constituents in the droplets). In addition to the requirements on the droplet library function and stability, the surfactant-in-oil solution must be coupled with the fluid physics and materials associated with the platform. Specifically, the oil solution must not swell, dissolve, or degrade the materials used to construct the microfluidic chip, and the physical properties of the oil (e.g., viscosity, boiling point, etc.) must be suited for the flow and operating conditions of the platform.

Droplets formed in oil without surfactant are not stable to permit coalescence, so surfactants must be dissolved in the fluorous oil that is used as the continuous phase for the emulsion library. Surfactant molecules are amphiphilic—part of the molecule is oil soluble, and part of the molecule is water soluble. When a water-oil interface is formed at the nozzle of a microfluidic chip for example in the inlet module described herein, surfactant molecules that are dissolved in the oil phase adsorb to the interface. The hydrophilic portion of the molecule resides inside the droplet and the fluorophilic portion of the molecule decorates the exterior of the droplet. The surface tension of a droplet is reduced when the interface is populated with surfactant, so the stability of an emulsion is improved. In addition to stabilizing the droplets against coalescence, the surfactant should be inert to the contents of each droplet and the surfactant should not promote transport of encapsulated components to the oil or other droplets.

The droplets comprised within the emulsion libraries of the present invention may be contained within an immiscible fluorocarbon oil which may comprise at least one fluorosurfactant. In some embodiments, the fluorosurfactant comprised within immiscible fluorocarbon oil is a block copolymer consisting of one or more perfluorinated polyether (PFPE) blocks and one or more polyethylene glycol (PEG) blocks. In other embodiments, the fluorosurfactant is a triblock copolymer consisting of a PEG center block covalently bound to two PFPE blocks by amide linking groups. The presence of the fluorosurfactant (similar to uniform size of the droplets in the library) is critical to maintain the stability and integrity of the droplets and is also essential for the subsequent use of the droplets within the library for the various biological and chemical assays described herein. Fluids (e.g., aqueous fluids, immiscible oils, etc.) and other surfactants that may be utilized in the droplet libraries of the present invention are described in greater detail herein.

The droplet libraries of the present invention are very stable and are capable of long-term storage. The droplet libraries are determined to be stable if the droplets comprised within the libraries maintain their structural integrity, that is the droplets do not rupture and elements do not diffuse from the droplets. The droplets libraries are also determined to be stable if the droplets comprised within the libraries do not coalesce spontaneously (without additional energy input, such as electrical fields described in detail herein). Stability may be measured at any temperature. For example, the droplets are very stable and are capable of long-term storage at any temperature; for example, e.g., −70° C., 0° C., 4° C., 37° C., room temperature, 75° C. and 95° C. Specifically, the droplet libraries of the present invention are stable for at least 30 days. More preferably, the droplets are stable for at least 60 days. Most preferably, the droplets are stable for at least 90 days.

The present invention provides an emulsion library which may comprise a plurality of aqueous droplets within an immiscible fluorocarbon oil which may comprise at least one fluorosurfactant, wherein each droplet is uniform in size and may comprise the same aqueous fluid and may comprise a different library element. The present invention also provides a method for forming the emulsion library which may comprise providing a single aqueous fluid which may comprise different library elements, encapsulating each library element into an aqueous droplet within an immiscible fluorocarbon oil which may comprise at least one fluorosurfactant, wherein each droplet is uniform in size and may comprise the same aqueous fluid and may comprise a different library element, and pooling the aqueous droplets within an immiscible fluorocarbon oil which may comprise at least one fluorosurfactant, thereby forming an emulsion library.

For example, in one type of emulsion library, all different types of elements (e.g., cells or beads), may be pooled in a single source contained in the same medium. After the initial pooling, the cells or beads are then encapsulated in droplets to generate a library of droplets wherein each droplet with a different type of bead or cell is a different library element. The dilution of the initial solution enables the encapsulation process. In some embodiments, the droplets formed will either contain a single cell or bead or will not contain anything, i.e., be empty. In other embodiments, the droplets formed will contain multiple copies of a library element. The cells or beads being encapsulated are generally variants on the same type of cell or bead. In one example, the cells may comprise cancer cells of a tissue biopsy, and each cell type is encapsulated to be screened for genomic data or against different drug therapies. Another example is that $10^{11}$ or $10^{15}$ different type of bacteria; each having a different plasmid spliced therein, are encapsulated. One example is a bacterial library where each library element grows into a clonal population that secretes a variant on an enzyme.

In another example, the emulsion library may comprise a plurality of aqueous droplets within an immiscible fluorocarbon oil, wherein a single molecule may be encapsulated, such that there is a single molecule contained within a droplet for every 20-60 droplets produced (e.g., 20, 25, 30, 35, 40, 45, 50, 55, 60 droplets, or any integer in between). Single molecules may be encapsulated by diluting the solution containing the molecules to such a low concentration that the encapsulation of single molecules is enabled. In one specific example, a LacZ plasmid DNA was encapsulated at a concentration of 20 fM after two hours of incubation such that there was about one gene in 40 droplets, where 10 μm droplets were made at 10 kHz per second. Formation of these libraries rely on limiting dilutions.

The present invention also provides an emulsion library which may comprise at least a first aqueous droplet and at least a second aqueous droplet within a fluorocarbon oil which may comprise at least one fluorosurfactant, wherein the at least first and the at least second droplets are uniform in size and comprise a different aqueous fluid and a different library element. The present invention also provides a method for forming the emulsion library which may comprise providing at least a first aqueous fluid which may comprise at least a first library of elements, providing at least a second aqueous fluid which may comprise at least a second library of elements, encapsulating each element of said at least first library into at least a first aqueous droplet within an immiscible fluorocarbon oil which may comprise at least one fluorosurfactant, encapsulating each element of said at least second library into at least a second aqueous droplet within an immiscible fluorocarbon oil which may comprise at least one fluorosurfactant, wherein the at least first and the at least second droplets are uniform in size and comprise a different aqueous fluid and a different library element, and pooling the at least first aqueous droplet and the at least second aqueous droplet within an immiscible fluorocarbon oil which may comprise at least one fluorosurfactant thereby forming an emulsion library.

Methods of the invention involve forming sample droplets. The droplets are aqueous droplets that are surrounded by an immiscible carrier fluid. Methods of forming such droplets are shown for example in Link et al. (U.S. patent application numbers 2008/0014589, 2008/0003142, and 2010/0137163), Stone et al. (U.S. Pat. No. 7,708,949 and U.S. patent application number 2010/0172803), Anderson et al. (U.S. Pat. No. 7,041,481 and which reissued as RE41, 780) and European publication number EP2047910 to Raindance Technologies Inc. The content of each of which is incorporated by reference herein in its entirety.

In certain embodiments, the carrier fluid may be caused to flow through the outlet channel so that the surfactant in the carrier fluid coats the channel walls. In one embodiment, the fluorosurfactant can be prepared by reacting the perflourinated polyether DuPont Krytox 157 FSL, FSM, or FSH with aqueous ammonium hydroxide in a volatile fluorinated solvent. The solvent and residual water and ammonia can be removed with a rotary evaporator. The surfactant can then be dissolved (e.g., 2.5 wt %) in a fluorinated oil (e.g., Flourinert (3M)), which then serves as the carrier fluid.

The system, as described in the present technique or any of its components, may be embodied in the form of a computer system. Typical examples of a computer system includes a general-purpose computer, a programmed microprocessor, a micro-controller, a peripheral integrated circuit element, and other devices or arrangements of devices that are capable of implementing the steps that constitute the method of the present technique.

The computer system may comprise a computer, an input device, a display unit and/or the Internet. The computer further comprises a microprocessor. The microprocessor is connected to a communication bus. The computer also includes a memory. The memory may include Random Access Memory (RAM) and Read Only Memory (ROM). The computer system further comprises a storage device. The storage device can be a hard disk drive or a removable storage drive such as a floppy disk drive, optical disk drive, etc. The storage device can also be other similar means for loading computer programs or other instructions into the computer system. The computer system also includes a communication unit. The communication unit allows the computer to connect to other databases and the Internet through an I/O interface. The communication unit allows the transfer as well as reception of data from other databases. The communication unit may include a modem, an Ethernet card, or any similar device which enables the computer system to connect to databases and networks such as LAN, MAN, WAN and the Internet. The computer system facilitates inputs from a user through input device, accessible to the system through I/O interface.

The computer system executes a set of instructions that are stored in one or more storage elements, in order to process input data. The storage elements may also hold data or other information as desired. The storage element may be in the form of an information source or a physical memory element present in the processing machine.

The set of instructions may include various commands that instruct the processing machine to perform specific tasks such as the steps that constitute the method of the present technique. The set of instructions may be in the form of a software program. Further, the software may be in the form of a collection of separate programs, a program module with a larger program or a portion of a program module, as in the present technique. The software may also include modular programming in the form of object-oriented programming. The processing of input data by the processing machine may be in response to user commands, results of previous processing or a request made by another processing machine.

Thus, an important aspect in developing this device will be to determine the flow rates, channel lengths, channel geometries, etc. that are required to properly time the arrival of the reagents released from the piezoelectric array with the "reaction chamber" droplets travelling in the orthogonal microfluidic channel. Once these design specifications are established, droplets containing random or specified reagent combinations can be generated on demand and merged with the "reaction chamber" droplets containing the samples/cells/substrates of interest.

Examples of a labeling substance which may be employed include labeling substances known to those skilled in the art, such as fluorescent dyes, enzymes, coenzymes, chemiluminescent substances, and radioactive substances as long as the label detects a double-stranded nucleic acid. Specific examples include radioisotopes (e.g., $^{32}$P, $^{14}$C, $^{125}$I, $^{3}$H, and $^{131}$I), fluorescein, rhodamine, dansyl chloride, umbelliferone, luciferase, peroxidase, alkaline phosphatase, β-galactosidase, β-glucosidase, horseradish peroxidase, glucoamylase, lysozyme, saccharide oxidase, microperoxidase, biotin, and ruthenium. In the case where biotin is employed as a labeling substance, preferably, after addition of a biotin-labeled antibody, streptavidin bound to an enzyme (e.g., peroxidase) is further added. Advantageously, the label intercalates within double-stranded DNA, such as ethidium bromide.

Advantageously, the label is a fluorescent label. The dye may be a DNA dye sold under the trade name EVAGREEN™, ROX™ or SYTOX™ orange. Examples of fluorescent labels include, but are not limited to, Atto dyes, 4-acetamido-4'-isothiocyanatostilbene-2,2'disulfonic acid; acridine and derivatives: acridine, acridine isothiocyanate; 5-(2'-aminoethyl)aminonaphthalene-1-sulfonic acid (EDANS); 4-amino-N-[3-vinyl sulfonyl)phenyl]naphthalimide-3,5 disulfonate; N-(4-anilino-1-naphthyl)maleimide; anthranilamide; BODIPY; Brilliant Yellow; coumarin and derivatives; coumarin, 7-amino-4-methylcoumarin (AMC, Coumarin 120), 7-amino-4-trifluoromethylcoumuarin (Coumarin 151); cyanine dyes; cyanosine; 4',6-diaminidino-2-phenylindole (DAPI); 5'S'-dibromopyrogallol-sulfonaphthalein (Bromopyrogallol Red); 7-diethylamino-3-(4'-isothiocyanatophenyl)-4-methylcoumarin;
diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansylchloride); 4-dimethylaminophenylazophenyl-4'-isothiocyanate (DABITC); eosin and derivatives; eosin, eosin isothiocyanate, erythrosin and derivatives; erythrosin B, erythrosin, isothiocyanate; ethidium; fluorescein and derivatives; 5-carboxyfluorescein (FAM), 5-(4,6-dichlorotriazin-2-yl)aminofluorescein (DTAF), 2',7'-dimethoxy-4'5'-dichloro-6-carboxyfluorescein, fluorescein, fluorescein isothiocyanate, QFITC, (XRITC); fluorescamine; IR144; IR1446; Malachite Green isothiocyanate; 4-methylumbelliferoneortho cresolphthalein; nitrotyrosine; pararosaniline; Phenol Red; B-phycoerythrin; o-phthaldialdehyde; pyrene and derivatives: pyrene, pyrene butyrate, succinimidyl 1-pyrene; butyrate quantum dots; Reactive Red 4 (Cibacron™ Brilliant Red 3B-A) rhodamine and derivatives: 6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas Red); N,N,N',N' tetramethyl-6-carboxyrhodamine (TAMRA); tetramethyl rhodamine; tetramethyl rhodamine isothiocyanate (TRITC); riboflavin; rosolic acid; terbium chelate derivatives; Cy3; Cy5; Cy5.5; Cy7; IRD 700; IRD 800; La Jolta Blue; phthalo cyanine; and naphthalo cyanine The fluorescent label may be a fluorescent protein, such as blue fluorescent protein, cyan fluorescent protein, green fluorescent protein, red fluorescent protein, yellow fluorescent protein or any photoconvertible protein. Colormetric labeling, bioluminescent labeling and/or chemiluminescent labeling may further accomplish labeling. Labeling further may include energy transfer between molecules in the hybridization complex by perturbation analysis, quenching, or electron transport between donor and acceptor molecules, the latter of which may be facilitated by double stranded match hybridization complexes. The fluorescent label may be a perylene or a terrylen. In the alternative, the fluorescent label may be a fluorescent bar code.

The present invention also encompasses a dye attached to a nucleic acid hydrolysis probe comprising an energy transfer moiety such as a second dye or quencher. The energy transfer moiety may be a second dye or a quencher. Advantageously, the hydrolysis probe may be a Taqman probe.

The labels allow for the quantitation of double-stranded DNA. The presence of a label indicates the presence of dsDNA. Because the reactions are partitioned into separate reactions, counting the number of labels directly correlates to the amount of dsDNA present. If the reactions are partitioned into droplets, then the dsDNA may be quantified by counting the number of labeled droplets. If the reactions are partitioned in a matrix, such as a gel, then the dsDNA may be quantified by counting the number of labeled spots in a gel. The gel may be a hydrogel, advantageously a acrylate gel, more advantageously an acrylate-dithiol gel, in particular a PEG acrylate-dithiol hydrogel. If the partitions are in an aqueous solution, the samples may be combined and quantified in a fluorimeter or spectrophotometer, for example. See, e.g., FIGS. 3-6.

In another embodiment, the present invention may also be utilized to determine if DNA contamination is present in reagents used for WGA analysis, such as to reduce WGA amplification bias. As mentioned previously, DNA contamination is a problem in WGA analysis, and especially in MDA reagents. Use of the invention would enable detection of DNA contamination.

In another embodiment, the present invention may also be utilized to reduce the incidence of chimeric sequences in the product mixture.

In another embodiment, the present invention may also be utilized as an analytical method to determine the number and or type of template molecules or contaminant molecules in a sample and/or in a preparative method to amplify a template or contaminant molecules in a sample prior to further analysis.

The present invention also encompasses preparative applications, such as, but not limited to, single genome amplification from single cells or purified nucleic acids, wherein material is recovered from the droplet or matrix for further analysis. The further analysis may be PCR and/or sequencing or any other characterization thereof.

In other embodiments, this method has applications in quality control of pharmaceuticals, biological and chemical reagents (especially DNA-modifying enzymes and assay components), as well as in characterization/quantification of DNA libraries, water quality testing, surveillance of industrial reactors, counter-bioterrorism, forensics, space exploration and astrobiology. The present invention is well-suited for analysis at the site of sample collection due to the low power requirements for isothermal incubation and straightforward interpretation of the raw data.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES

Example 1: Microfluidic Droplets

Fabricating the microfluidic devices. Microfluidic devices were constructed using standard PDMS soft lithography (McDonald J C, et al. (2000) Fabrication of microfluidic systems in poly(dimethylsilox-ane). Electrophoresis 21:27-40) with 18 micron SU8-on-Si wafer molds formed using transparency masks from FineLine Imaging. After curing, the PDMS device is adhered to glass for 2 hours at 80° C.

Multiple displacement reaction. The MDA reactions were prepared according to protocol (Qiagen Repli-G Midi Kit) with Lambda DNA added to 5e-5, 5e-4, and 5e-3 ng/µL in the standard samples. Each reaction was supplemented with 0.3% of the surfactant TWEEN™-20 and the DNA dye EVAGREEN™ prior to drop formation. Drop and bulk samples incubated at 30° C. for 16 h, and 65° C. for 20 m. Half of the post-incubation drop samples were converted to bulk with half volume 1H,1H,2H,2H-Perfluoro-1-octanol (Sigma Aldrich) and half of the post-incubation bulk samples were made into drops.

Forming monodisperse droplets. Monodisperse aqueous drops were formed in fluorocarbon oil using a flow-focusing microfluidic device. Premixed aqueous sample was directed to the middle inlet of a cross-shaped drop-making junction. A 4 inHg vacuum on the outlet induced drop formation. The resistances of the three junction inlets determined the flow rate ratio between the oil and aqueous phases, and were optimized to produce 50 um diameter drops.

Quantitative polymerase chain reaction. The bulk or droplet-to-bulk reactions were diluted 1:200 and used as template in qPCR with an equal volume of Jumpstart Taq ReadyMix (Sigma-Aldrich). Each reaction received primers (5'-AGTGCCGAATCACGCCGCAA-3' and 5'-AGTGTGTGCGTCGCTGCCAT-3') to 0.2 µM and DNA dyes sold under the trade names EVAGREEN™ and ROX™.

Imaging. Images were taken with a Canon EOS Rebel 60D mounted on a Nikon epi-fluorescent microscope with a 10× air objective at 0 and 16 hours. Zero hour samples were heat-killed at 65° C. for 20 m before imaging.

Figure 2:
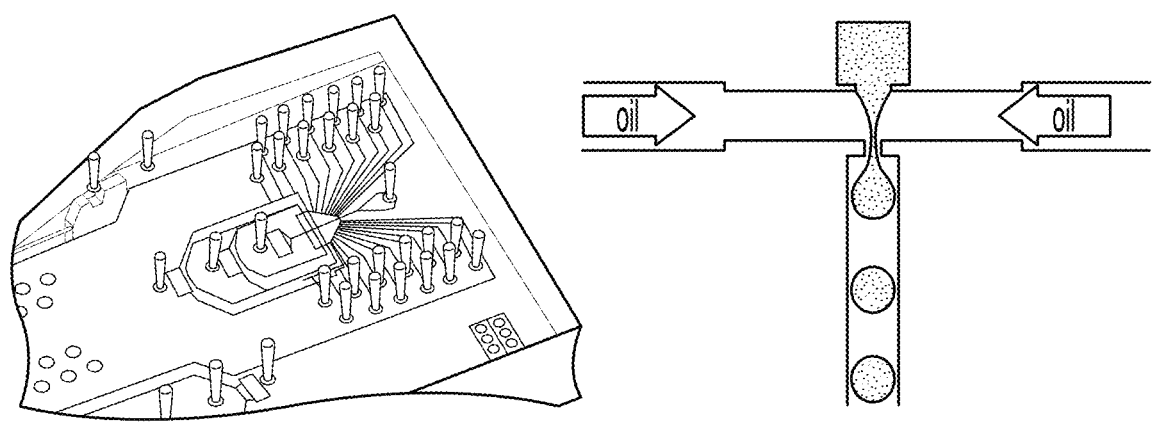
FIG. 2 depicts a microfluidic device for forming monodisperse droplets. Droplet formation can be driven by positive flow from the inlets, vacuum from the outlet (1) or peristaltic pumping of the dispersed phase.

FIGS. 1 and 2 depict MDA reactions in droplets with lambda phage genome as a template, which is representative of single genome amplification as well as single cell analysis.

FIG. 1 depicts MDA reactions with appropriate template concentrations were prepared using a Qiagen Repli-G Midi kit according to the manufacturer's protocol (Qiagen, Valencia, Calif.), and supplemented with the DNA dye EVAGREEN™. Monodisperse droplets were formed in a flow-focusing microfluidic device with fluorinated oil continuous phase and incubated at 30 C for 16 h.

FIG. 2 depicts a microfluidic device for forming monodisperse droplets. Droplet formation can be driven by positive flow from the inlets, vacuum from the outlet (1) or peristaltic pumping of the dispersed phase.

Example 2: Hydrogel Matrices

FIGS. 3-6 depict MDA reactions in a gel matrix with lambda phage genome as a template, which is representative of single genome amplification as well as single cell analysis.

Figure 3:
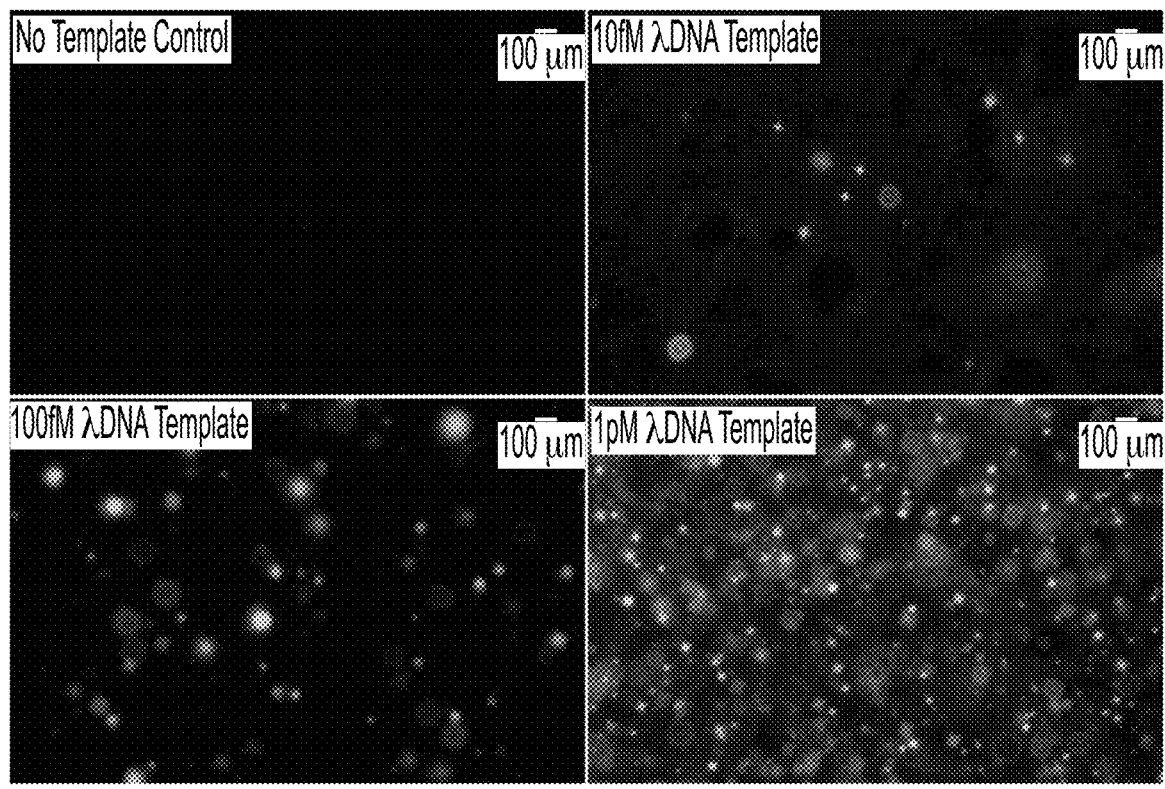
FIG. 3 depicts digital MDA products at 30° C. after 16 hours stained with 500 nM of the DNA dye SYTOX™ Orange in 7% 4-Arm PEG Acrylate-Dithiol hydrogels, with each spot corresponding to a single lambda phage genome amplified separately in the gel. The initial Lambda Phage DNA template concentrations were 10 fM, 100 fM, and 1 pM. (corresponding to 1.3e-5 ng/μL, 1.3e-4 ng/μL, and 1.3e-3 ng/μL).

FIG. 3 depicts digital MDA products at 30° C. after 16 hours stained with 500 nM of the DNA dye SYTOX™ Orange in 7% 4-Arm PEG Acrylate-Dithiol hydrogels. The initial Lambda Phage DNA template concentrations were 10 fM, 100 fM, and 1 pM. (or convert to mass/volume, 1.3e-5 ng/µL, 1.3e-4 ng/µL, and 1.3e-3 ng/µL).

Figure 4:
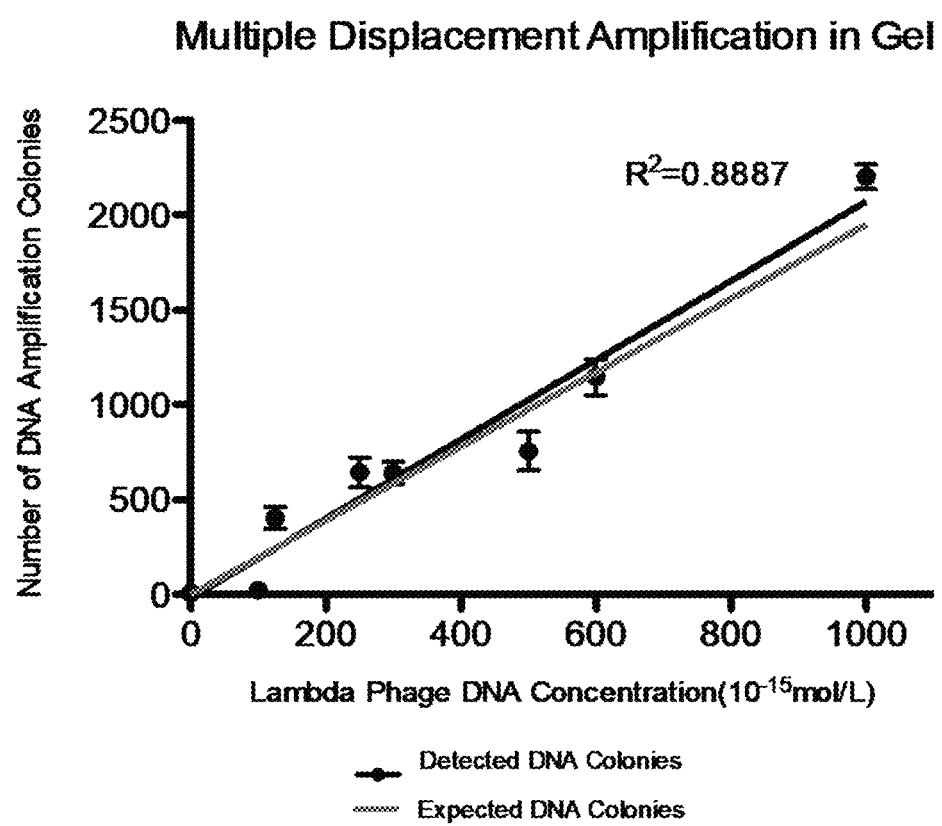
FIG. 4 depicts the number of DNA amplification colonies observed vs. initial lambda phage DNA concentration in 4-arm PEG acrylate gel after 16 hours of multiple displacement amplification. DNA was stained with 500 nM of the DNA dye SYTOX™ Orange.

FIG. 4 depicts a multiple displacement amplification in gel. The figure depicts the number of DNA amplification colonies observed vs. initial lambda phage DNA concentration in 4-arm PEG acrylate gel after 16 hours of multiple displacement amplification. DNA was stained with 500 nM of the DNA dye SYTOX™ Orange.

Figure 5:
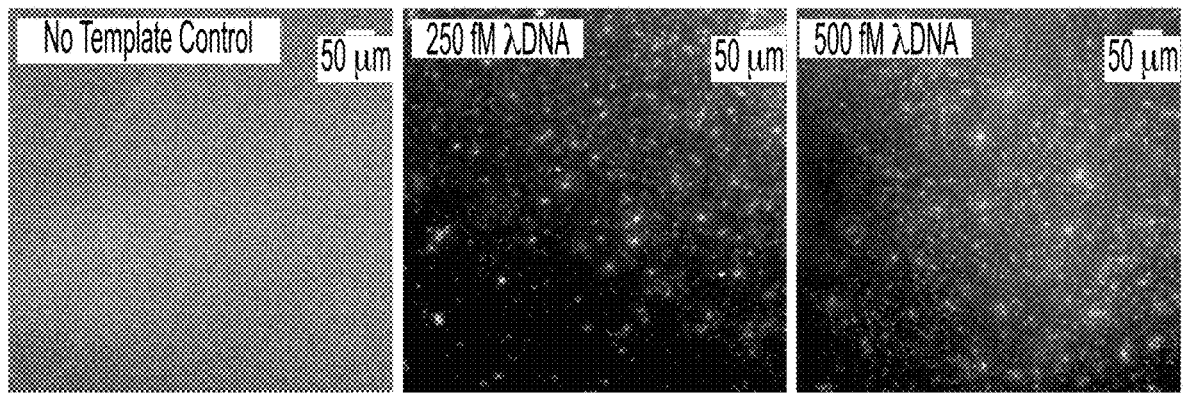
FIG. 5 depicts 216 bp PCR products using Vent(exo-) polymerase after 40 thermal cycles stained with 500 nM of the DNA dye SYTOX™ Orange dye in 7% 4-Arm PEG Acrylate-Dithiol hydrogels. The initial Lambda Phage DNA template concentrations were 250 fM and 500 fM. Each spot in the gel corresponds to a single lambda phage genome template molecule.

FIG. 5 depicts 216 bp PCR products using Vent(exo-) polymerase (a polymerase with strong strand displacement) after 40 thermal cycles stained with 500 nM of the DNA dye SYTOX™ Orange dye in 7% 4-Arm PEG Acrylate-Dithiol hydrogels. The initial Lambda Phage DNA template concentrations were 250 fM and 500 fM.

Figure 6:
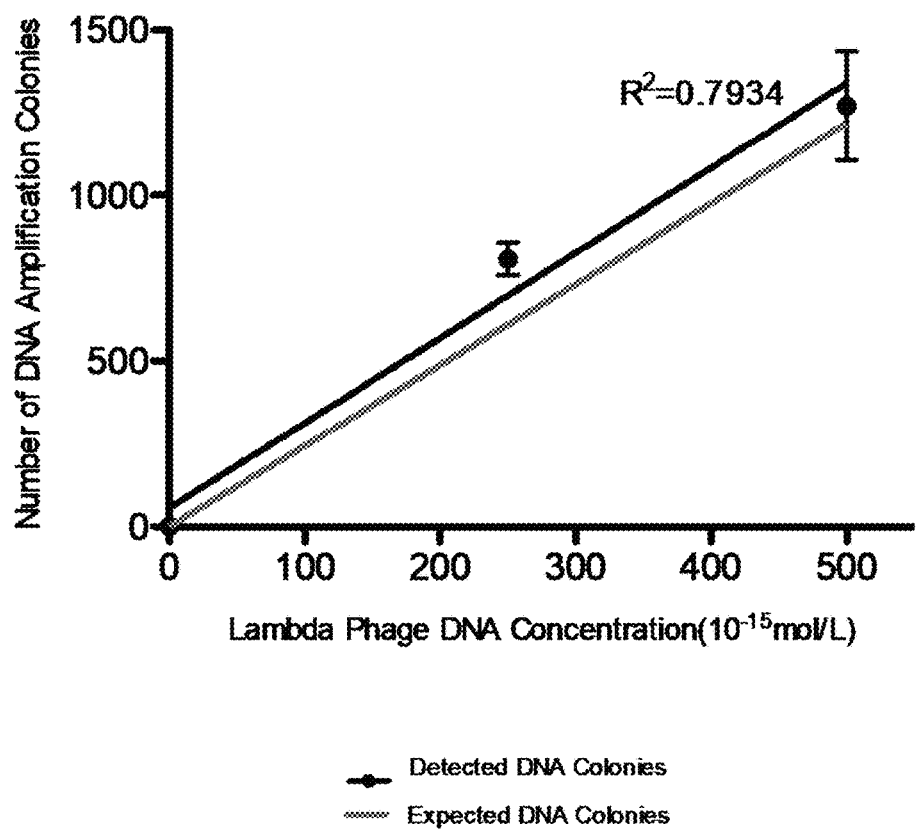
FIG. 6 depicts the number of DNA amplification colonies observed vs. initial lambda phage DNA concentration after 40 cycles of thermocycling. DNA was stained with 500 nM of the DNA dye SYTOX™ Orange.

FIG. 6 depicts the number of DNA amplification colonies observed vs. initial lambda phage DNA concentration after 40 cycles of thermocycling. DNA was stained with 500 nM of the DNA dye SYTOX™ Orange.

Example 3: Materials and Methods

4-Arm PEG Hydrogel. Hydrogel components, including 4-arm PEG acrylate (MW 10,000) and HS-PEG-SH (MW 3,400), were obtained from Layson Bio. For every 25 µl of 10% weight percentage cross-linked hydrogel, 1.6 mg of 4-arm PEG acrylate and 1.1 mg of HS-PEG-SH were dissolved in PBS buffer (Invitrogen). It was briefly vortexed and centrifuged to ensure mixing and it was allowed to sit for 10 minutes while the hydrogel components cross-linked through the reaction between the thiol and acrylate groups Polymerase Chain Reaction (PCR). The primers used for PCR on purified λ DNA (48 kbp, NEB) were purchased from IDT. Primer F 5': CGGCAAACGGGAAT-GAAACGCC. Primer R 5': TGCGGCAAA-GACAGCAACGG. A 25 µl hydrogel PCR reaction consisted of 2U of VentR(exo-) polymerase (NEB), 1× ThermoPol Reaction Buffer (NEB), 0.4 mM dNTP (NEB), 1 µM Primers, 5% DMSO (Sigma), 0.5 mg/ml BSA (NEB), 1.6 mg 4-arm PEG acrylate in PBS, 1.1 mg HS-PEG-SH in PBS, and DNA template (NEB) of various concentrations. The 25 µl above components were loaded in a 9 mm by 9 mm frame-seal chamber (Bio-rad). The following thermal protocol was ran on MJ Research PTC-100 twin tower (model number of the tower block) thermal cycler: 30° C. for 30 min (gel polymerization), 98° C. for 3 min; 98° C. for 30 sec, 57° C. for 30 sec, 72° C. for 1 min for 40 to 60 cycles; 72° C. for 5 min and hold at 4° C. The gel was stained with 500 nM of the DNA dye SYTOX™ Orange nucleic acid dye (Invitrogen).

Multiple Displacement Amplification (MDA). A 25 µl hydrogel MDA reaction consisted of 0.5 µl of REPLI-g sc Polymerase (Qiagen), 1× Phi 29 buffer (NEB), 50 µM Random Hexamers (IDT), 2.5% DMSO, 0.4 mM dNTP, 0.5 mg/ml BSA, 500 nM of the DNA dye SYTOX™ Orange (Invitrogen) and denatured λDNA. DNA was denatured (alkaline buffer "D1", Qiagen) and neutralized (buffer "N1", Qiagen), prior to encapsulation. All MDA and gel components, except polymerase and the DNA dye SYTOX™ Orange, were UV treated for 30 min using a UV crosslinker (Stratalinker, Stratagene) to render contaminating background DNA incompetent for MDA. The gel was sealed in the chamber and maintained at 30° C. for 8 hours or longer.

Real Time MDA in Hydrogel. The above MDA in hydrogel was conducted at room temperature for 8 hours on a Nikon Eclipse Ti Epi-Fluorescent Microscope excited with a Lumencor Spectra X light engine (Lumencor) and filtered through a SpGold filter (Semrock). MATLAB was used to capture time-lapse image stacks through a Nikon 20×/0.4 objective, and Hamamatsu C11440 camera with 15 min intervals, 100 ms exposure time and 10% Lumencor light power.

Microbes MDA in Hydrogel. *Staphylococcus Aureus* (GFP) RN6390 and *Escherichia. coli* (RFP) BL21 strains were obtained as cryogenic stocks. For each culture, 5 ml LB broth was inoculated from the stock and cultured at 30° C. for 12 hours. 500 µl of each culture (O.D. 600 nm=0.4) were centrifuged for 2 min at >10 krpm and the pellet was washed with 500 µl PBS twice. A 25 µl hydrogel MDA reaction on microbes consisted of the components listed (treated with UV, except Polymerase) in addition to different concentrations and mixtures of microbes. The cross-linked hydrogels were heated to 95° C. for 5 min in order to lyse and denature microbes. Polymerase was added on top of the hydrogel after denaturation and MDA was conducted for 8 hours or more.

Product Retrieval. Targeted clusters labelled with FISH in hydrogel were retrieved using an AVISO CellSelector (ALS-Jena) with a 50 µm diameter glass capillary (ALS-Jena). The picking was conducted with parameter settings described in photos below. The glass capillary was filled and rinsed with PBS with 2% of the surfactant TWEEN™20 before every pick. Microsamples were deposited in 5 µl of lysis buffer (1 M KOH, 5 mM EDTA). Hydrogel clusters dissolved after being heated at 70° C. for 5 min in the lysis buffer and neutralized with 5 µl of "stop solution" (Qiagen). The neutralized DNA product was used for subsequent PCR, MDA, and whole genome sequencing analysis.

Figures 7A, 7B:
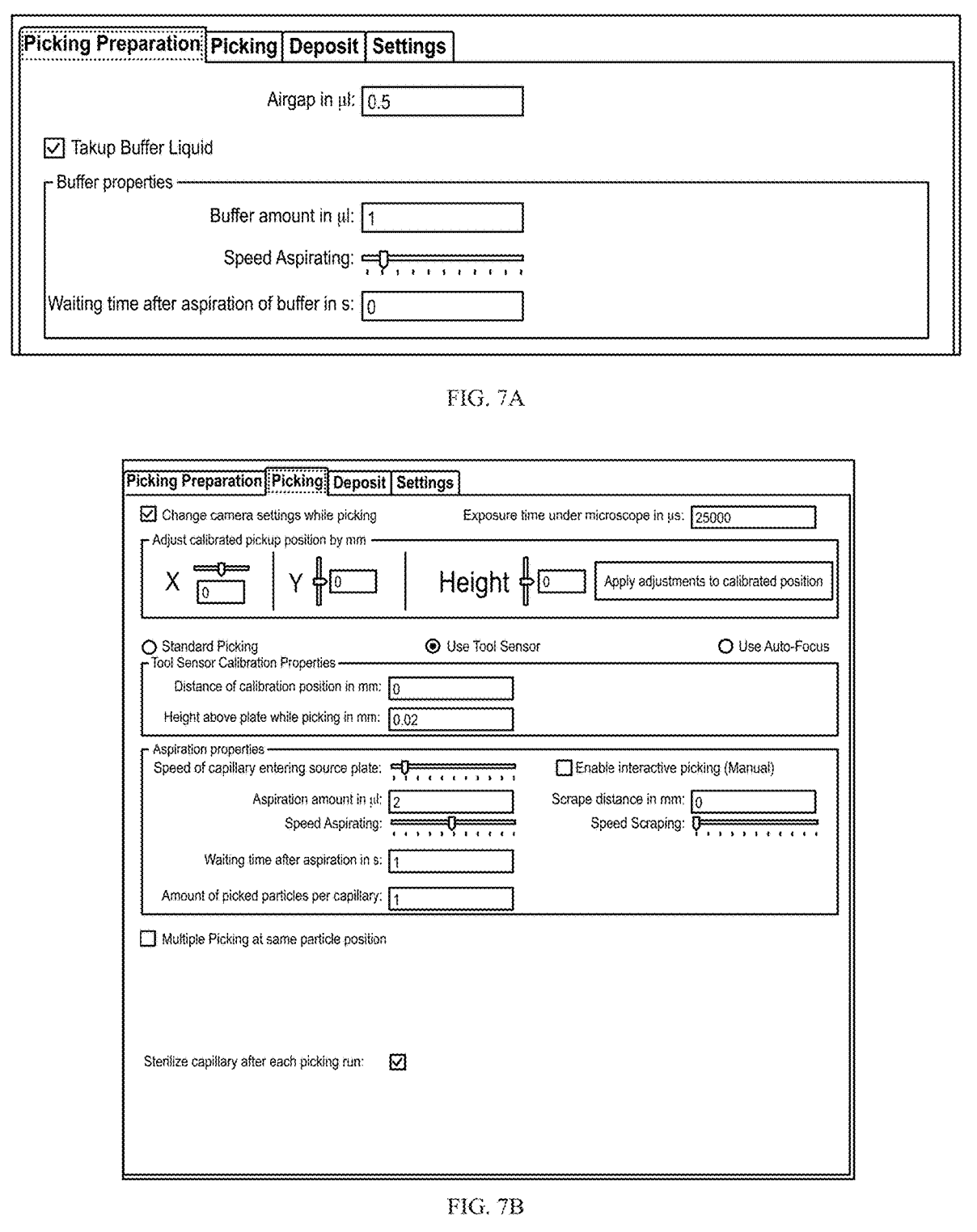

FIG. 7A depicts a picking preparation. Glass capillary is preloaded with 1 ul of 2% PBST (PBS with the surfactant TWEEN™ 20) buffer with an air gap of 0.5 ul between the system oil.

FIG. 7B depicts picking. Tool sensor on was turned on, which detects the hard glass slide surface and signals glass capillary the right picking position. Capillary was elevated for 20 um before aspirating. 2 ul of hydrogel cylinder was retrieved in capillary for depositing.

FIG. 7C depicts deposit. The hydrogel cylinder was dispensed into a PCR 96 tube well filled with 10 ul of lysis buffer. Maximum air gap was dispensed and the capillary was rinsed 5 times to ensure complete dispensing.

FIG. 7D depicts setting. After picking and depositing, the capillary is sterilized with 3 ul of 2% PBST for 2 loops with a 5 sec of waiting time in between.

Example 4: Results and Discussion

A goal was to accurately quantify single genetic targets in hydrogel. In order to achieve this goal, amplifications on purified Lambda phage DNA in hydrogel was tested. There are increasing PCR cluster counts vs increasing initial DNA template concentration in hydrogel. This was a fundamental experiment to demonstrate the feasibility of PCR in PEG hydrogel. The DNA concentration represents the initial 1 µl template input in a 25 µl hydrogel. The expected number of clusters per field of view was calculated based on the thickness of a frame-seal chamber (308 µm) and the initial DNA concentration. The SEM bar is based on ten different fields of views for the same frame-seal chamber sample at each concentration. Cluster was counted using Imaris software.

Figure 8:
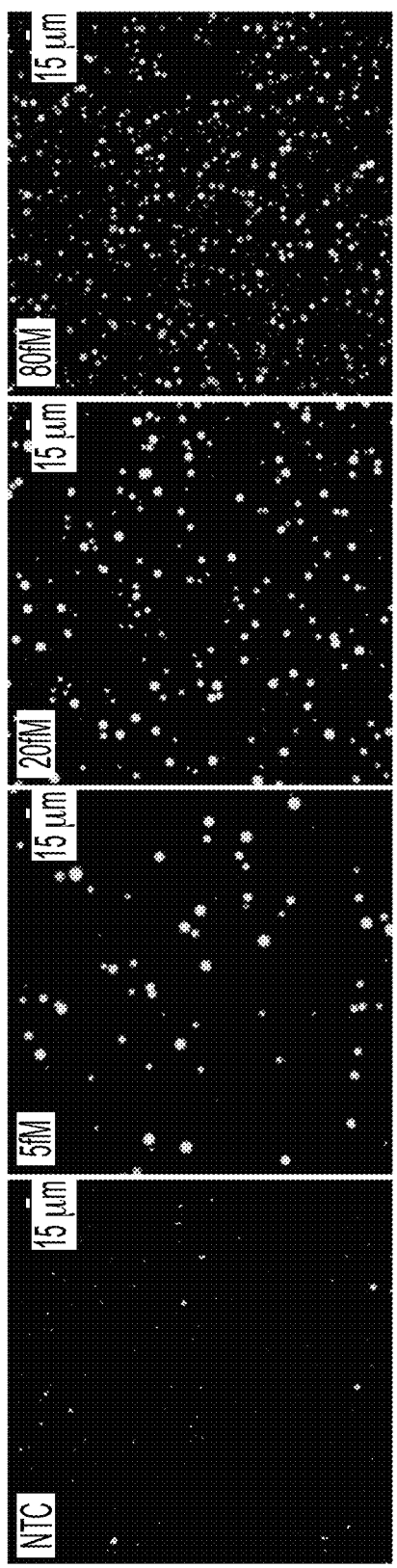
FIG. 8 depicts increasing MDA cluster counts versus increasing initial DNA template concentration.
Figure 9:
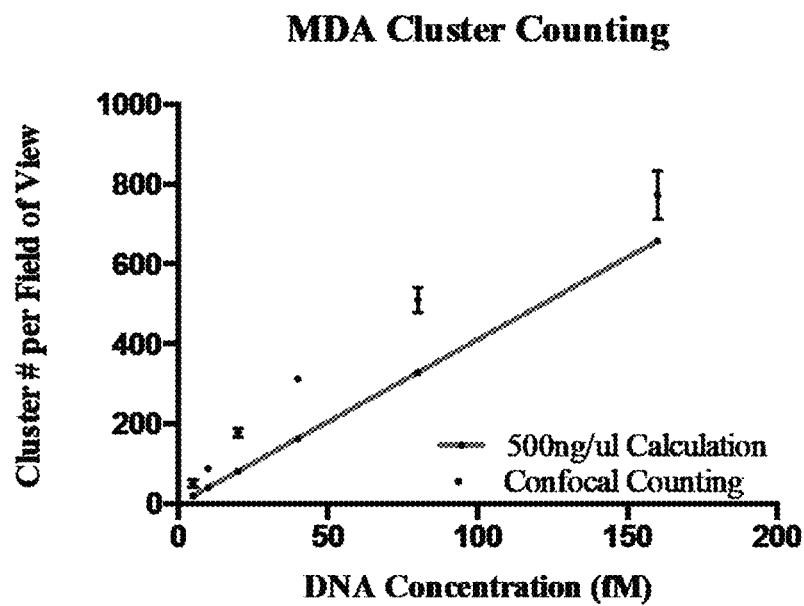
FIG. 9 depicts a solid phase MDA calibration curve.

Accurate quantification of DNA was evaluated by whole genome amplification-MDA in hydrogel. FIG. 8 displays increasing MDA cluster counts vs increasing initial DNA template concentration in 8% hydrogel after 8 hours of MDA reaction. Each figure was a z axis max projection from a confocal stack taken by a Nikon ultra-fast laser scanning confocal microscope. FIG. 9 shows the calibration curve obtained from MDA reaction in gel. The SEM bar was based on two different fields of views for frame-seal samples of each initial DNA concentration. The over-estimating parabolic curve of the counting resulted from DNA fragmentation and image analysis limitation at high DNA concentration.

Figure 10:
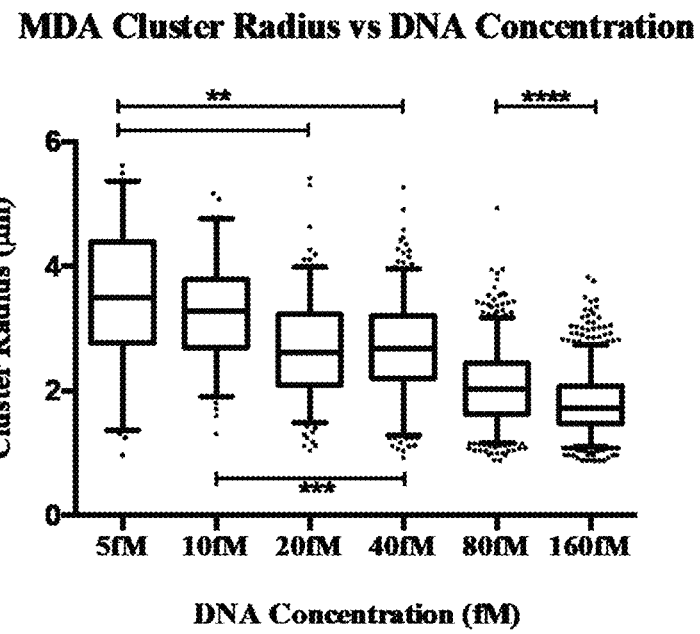
FIG. 10 depicts a cluster radius characterization where ** is P<0.01.

DNA cluster characterizations. Key experiment parameters, such as template concentration, gel percentage, primer acrydite modification, were manipulated to further categorize the DNA cluster properties. FIG. 10 shows that the cluster radius (5%-95%) had a decreasing trend when the DNA concentration was increased. One hypothesis was that in a 25 µl frame-seal chamber, there were limited dNTP, hexamers, and DNA polymerase. When more DNA molecules are competing with the neighboring DNA for resources for amplification, the more DNA there was, the less resources each cluster was able to get. This hypothesis was not supported with experiments that incorporate extra reagents for a fixed reaction time.

Figure 11:
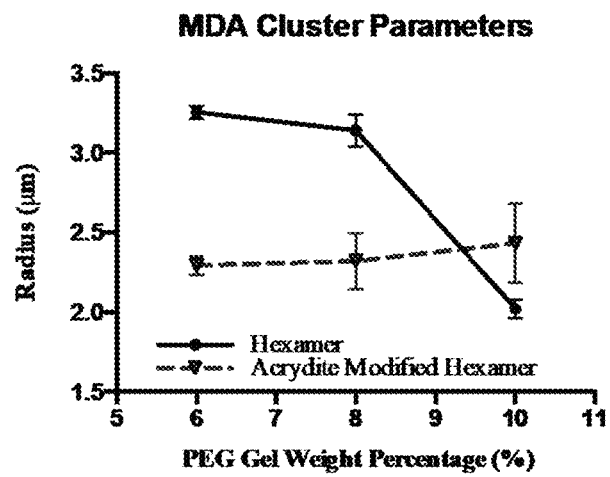
FIG. 11 depicts MDA cluster size characterization where increasing hydrogel weight percentage and hexamer modification decreased DNA cluster radius.

Adding primer modification was implemented to manipulate the size of the DNA cluster. FIG. 11 shows the trend of acrydite-modified primers' effect on the final MDA cluster size. Hexamers were linked to the thiol group and was incorporated in the hydrogel network, thus limiting the movement of final DNA product and reducing the cluster radius. The cluster size also correlated with gel weight percentage, as weight percentage determined the pore size of hydrogel and the diffusion limitation on DNA products.

Figure 12:
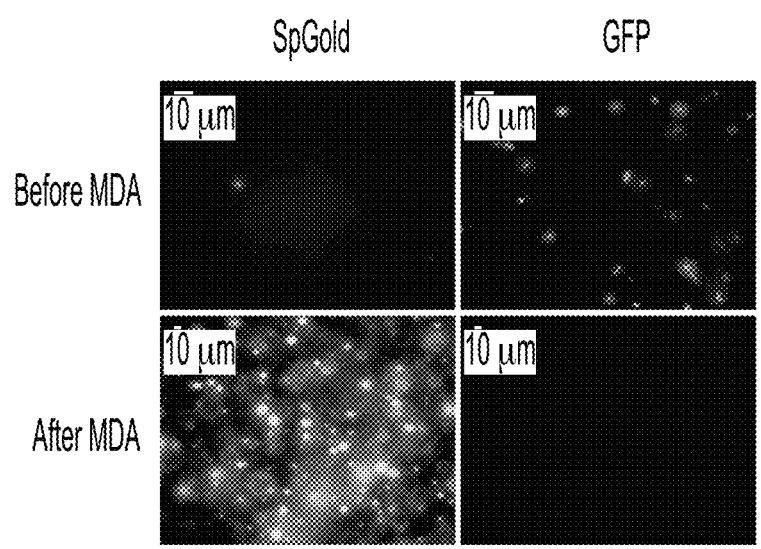
FIG. 12 depicts a solid phase single *E. coli* MDA.

Single *E. coli* whole genome amplification by MDA. *E. coli* with GFP fluorescence were encapsulated in hydrogels and kept alive until heat lysis. As is shown by FIG. 12, single *E. coli* were identified under blue light excitation before heat lysis in hydrogel. After 5 minutes of heat lysis at 95° C. and 8 hours of MDA reaction at 30° C., many DNA clusters were observed stained with the DNA dye SYTOX™ Orange through a SpGold filter.

Figure 13A:
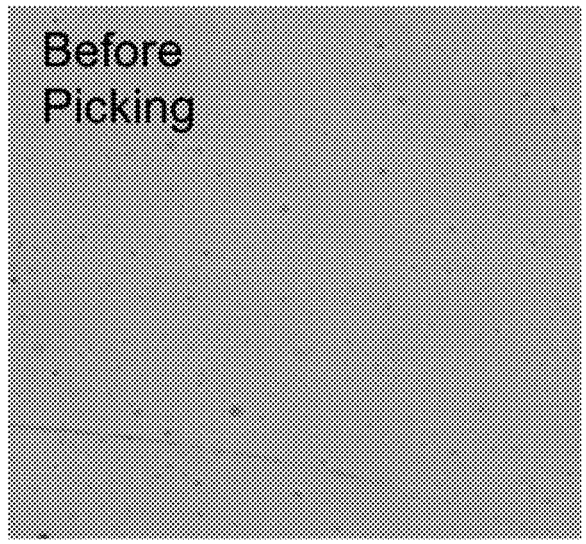
FIG. 13A depicts a before picking microsample.
Figure 13B:
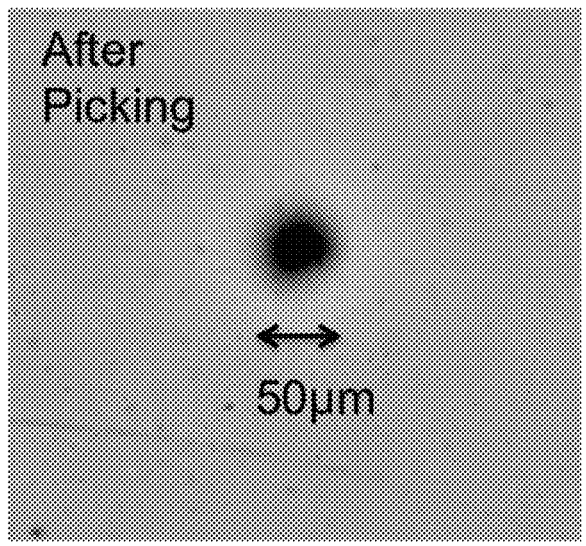
FIG. 13B depicts an after picking microsample.

FIG. 13 depicts a before and after picking microsample.

The invention is further described by the following numbered paragraphs:

1. A method of quantifying a nucleic acid comprising (a) contacting a sample to be tested with whole-genome amplification (WGA) reaction components and a dye molecule or other probe to form a reaction sample, wherein the dye molecule detects the nucleic acid; (b) partitioning the reaction sample wherein each partitioned reaction sample corresponds to a single reaction; (c) allowing the reaction to occur in the partitioned reaction sample and (d) determining the number of partitioned reaction samples having the dye molecule, wherein the dye molecule indicates the presence of the nucleic acid; thereby quantifying the nucleic acid is quantitated in the sample to be tested.

2. The method of numbered paragraph 1, wherein the nucleic acid is selected from the group consisting of double stranded DNA, single stranded DNA, single stranded RNA or PNA.

3. The method of numbered paragraph 1 or 2, wherein the WGA is carried out by multiple displacement amplification (MDA).

4. The method of numbered paragraph 3, wherein the WGA reaction components are from a commercial MDA kit.

5. The method of numbered paragraph 4, wherein the commercial MDA kit selected from the group consisting of Repli-G Midi (Qiagen), GenomiPhi (GE) and RepliPHI (Epicentre).

6. The method of any one of numbered paragraphs 1-5, wherein the WGA reaction components further comprise an emulsion component.

7. The method of numbered paragraph 6, wherein the emulsion component is an inert oil.

8. The method of numbered paragraph 7, wherein the oil is a fluorocarbon oil or perfluoropolyether.

9. The method of any one of numbered paragraphs 1-8, wherein the partitioned reaction sample is a droplet.

10. The method of numbered paragraph 9, wherein the droplet is a monodisperse aqueous droplet.

11. The method of any one of numbered paragraphs 1-8, wherein the partitioned reaction sample is in a matrix.

12. The method of numbered paragraph 11, wherein the matrix is a gel.

13. The method of numbered paragraph 12, wherein the gel is a hydrogel.

14. The method of numbered paragraph 13, wherein the hydrogel comprises a polyethylene glycol, a peptide, a protein, a polysaccharide, a synthetic polymer, a natural polymer and/or a block copolymer.

15. The method of any one of numbered paragraphs 1-14, wherein the WGA reaction is supplemented with a surfactant.

16. The method of numbered paragraph 15, wherein the surfactant is that sold under the trade name TWEEN™, TRITON™, SPAN™, or PLURONIC™, a poly(ethylene glycol)-containing molecule or a perfluropolyether-containing molecule.

17. The method of numbered paragraph 16, wherein the TWEEN™ surfactant is 0.3% TWEEN™-20.

18. The method of any one of numbered paragraphs 1-17, wherein the reaction occurs in the partitioned reaction sample at 30° C.

19. The method of any one of numbered paragraphs 1-17, wherein the reaction occurs in the partitioned reaction sample at 65° C.

20. The method of any one of numbered paragraphs 1-19, further comprising a heat lysis reaction.

21. The method of numbered paragraph 20, wherein the heat lysis reaction is at 95° C.

22. The method of any one of numbered paragraphs 1-21, wherein the dye molecule is an intercalating dye.

23. The method of any one of numbered paragraphs 1-22, wherein the dye is a fluorescent dye.

24. The method of numbered paragraph 23, wherein the dye is an EVAGREEN™ DNA dye.

25. The method of numbered paragraph 23, wherein the dye is a ROX™ DNA dye.

26. The method of numbered paragraph 23, wherein the dye is a SYTOX™ Orange DNA dye.

27. The method of any one of numbered paragraphs 1-26, wherein the dye is attached to a nucleic acid hydrolysis probe comprising an energy transfer moiety such as a second dye or quencher.

28. The method of numbered paragraph 27, wherein the energy transfer moiety is a second dye or a quencher.

29. The method of numbered paragraph 28, wherein the quencher is a Taqman probe.

30. The method of any one of numbered paragraphs 1-29, wherein the method further comprises recovering material from the droplet or matrix for further analysis.

31. The method of numbered paragraph 30, wherein the further analysis is PCR or sequencing.

32. The method of any one of numbered paragraphs 1-31, wherein the sample to be tested is a bacteria.

33. The method of numbered paragraph 32, wherein the bacteria is a *Staphylococcus Aureus* or an *Escherichia coli*.

34. The method of any one of numbered paragraphs 1-33 wherein the method reduces WGA amplification bias.

35. The method of any one of numbered paragraphs 1-34 wherein the method reduces incidence of chimeric sequences.

36. The method of any one of numbered paragraphs 1-35 wherein the method is used as an analytical method to determine the number and or type of template molecules or contaminant molecules in a sample.

37. The method of any one of numbered paragraphs 1-35 wherein the method is a preparative method to amplify a template or contaminant molecules in a sample prior to further analysis.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A method of quantifying a nucleic acid molecule, the method comprising:
   (a) contacting a sample to be tested with degenerate oligonucleotide primers, a DNA polymerase, and a label that detects nucleic acid molecules to form a reaction sample;
   (b) partitioning the reaction sample at limiting dilution into monodisperse droplets, wherein each droplet corresponds to a single nucleic acid molecule amplification reaction comprising a nucleic acid molecule or no nucleic acid molecule;
   (c) allowing the nucleic acid molecule amplification reaction to occur in the droplets; and
   (d) determining the number of droplets comprising nucleic acid molecules by detecting the label;
   thereby quantifying the nucleic acid molecule in the sample to be tested.

2. The method of claim 1, wherein the nucleic acid molecule is selected from the group consisting of double stranded DNA, single stranded DNA, single stranded RNA, and PNA.

3. The method of claim 1, wherein the nucleic acid amplification reaction is a multiple displacement amplification reaction.

4. The method of claim 1, wherein the reaction sample further comprises an emulsion component.

5. The method of claim 1, wherein the nucleic acid molecule amplification reaction is supplemented with a surfactant.

6. The method of claim 1, wherein the reaction occurs in the nucleic acid molecule amplification reaction droplets at 30° C., or wherein the reaction occurs in the nucleic acid molecule amplification reaction droplets at 65° C.

7. The method of claim 1, further comprising a heat lysis reaction.

8. The method of claim 1, wherein the label is an intercalating dye.

9. The method of claim 1, wherein the label is a fluorescent dye.

10. The method of claim 1, wherein the label is attached to a nucleic acid hydrolysis probe comprising an energy transfer moiety, wherein the energy transfer moiety is a second dye or quencher.

11. The method of claim 1, wherein the method further comprises recovering material from one of the monodisperse droplets for further analysis.

12. The method of claim 1, wherein the sample to be tested comprises bacteria.

13. The method of claim 1, wherein the method reduces nucleic acid molecule amplification bias, reduces incidence of chimeric nucleic acid molecules, is used as an analytical method to determine the number and/or type of nucleic acid molecules or contaminant molecules in a sample, or is a preparative method to amplify a nucleic acid molecule in a sample prior to further analysis.

14. A method of amplifying a nucleic acid molecule in a sample, the method comprising:
(a) contacting a sample with degenerate oligonucleotide primers, a polymerase, and a label that detects nucleic acid molecules to form a reaction sample;
(b) partitioning the reaction sample at limiting dilution into a hydrogel; and
(c) allowing the amplification reaction to occur in the hydrogel.

15. The method of claim 14, wherein the hydrogel comprises a peptide, a protein, a polysaccharide, a synthetic polymer, a natural polymer and/or a block copolymer.

16. The method of claim 14, wherein the method further comprises recovering a nucleic acid cluster from the hydrogel for further analysis.

17. The method of claim 14, wherein the method reduces nucleic acid molecule amplification bias, reduces incidence of chimeric nucleic acid molecule sequences, or is used as an analytical method to determine type of nucleic acid molecules or contaminant molecules in a sample.

18. The method of claim 14, further comprising detecting labelled nucleic acid clusters within the hydrogel to quantify the nucleic acid molecules in the sample, and/or determining the cluster radius, cluster size, or optical intensity of the labelled nucleic acid clusters.

19. A method of preparing nucleic acid molecules for analysis, the method comprising:
(a) contacting a sample to be tested with degenerate oligonucleotide primers, a DNA polymerase, and a label that detects nucleic acid molecules to form a reaction sample;
(b) partitioning the reaction sample into monodisperse droplets, wherein each droplet corresponds to a single nucleic acid amplification reaction comprising a nucleic acid molecule or no nucleic acid molecule; and
(c) allowing the nucleic acid amplification reaction to occur in the droplets.

20. The method of claim 4, wherein the emulsion component is an inert oil.

21. The method of claim 20, wherein the inert oil is a fluorocarbon oil or perfluoropolyether.

22. The method of claim 7, wherein the heat lysis reaction is at 95° C.

23. The method of claim 10, wherein the quencher is a Taqman probe.

24. The method of claim 11, wherein the further analysis is PCR or sequencing.

* * * * *